United States Patent [19]

Tamada et al.

[11] Patent Number: 5,034,395
[45] Date of Patent: Jul. 23, 1991

[54] DIHYDROPYRIDINE DERIVATIVES

[75] Inventors: Shigeharu Tamada; Kazuyoshi Nagami; Shuji Teramoto, all of Tokushima; Tatsuyoshi Tanaka, Sapporo; Kazuyuki Nakagawa, Tokushima, all of Japan

[73] Assignee: Otsuka Pharmaceutical Co., Ltd., Tokyo, Japan

[21] Appl. No.: 18,836

[22] Filed: Feb. 24, 1987

Related U.S. Application Data

[63] Continuation of Ser. No. 677,364, Nov. 30, 1984, abandoned.

[30] Foreign Application Priority Data

Dec. 2, 1983 [JP]  Japan ............................ 58-228880

[51] Int. Cl.$^5$ .......................................... A61K 31/435
[52] U.S. Cl. .................................... 514/277; 514/315; 514/336; 514/343; 546/321; 546/263; 546/275; 546/283; 546/284; 546/256
[58] Field of Search ............... 544/365; 546/321, 263, 546/256, 275, 276, 283, 284; 514/252, 332, 356, 277, 315, 336, 343

[56] References Cited

U.S. PATENT DOCUMENTS

| | | | |
|---|---|---|---|
| 3,664,627 | 2/1972 | Bossert | 514/356 |
| 3,905,970 | 9/1975 | Bossert | 544/364 |
| 3,985,758 | 10/1976 | Minakami | 546/321 |
| 4,044,141 | 8/1977 | Bossert | 546/193 |
| 4,393,070 | 7/1983 | Sato | 514/356 |
| 4,430,333 | 2/1984 | Campbell | 544/360 |
| 4,532,248 | 7/1985 | Franckowiak | 514/222 |
| 4,578,395 | 3/1986 | Yamaguchi | 514/356 |
| 4,622,332 | 11/1986 | Wehinger | 546/283 |
| 4,656,181 | 4/1987 | Sunkel | 544/365 |
| 4,672,068 | 6/1987 | Kutsuma | 546/283 |

FOREIGN PATENT DOCUMENTS

| | | |
|---|---|---|
| 0026317 | 4/1981 | European Pat. Off. . |
| 0063359 | 10/1982 | European Pat. Off. . |
| 0063747 | 11/1982 | European Pat. Off. . |
| 0161877 | 11/1982 | European Pat. Off. . |
| 0088903 | 9/1983 | European Pat. Off. . |
| 0094159 | 11/1983 | European Pat. Off. ............ 544/360 |
| 0173126 | 3/1986 | European Pat. Off. . |
| 2844782 | 4/1972 | Fed. Rep. of Germany . |
| 2117572 | 10/1972 | Fed. Rep. of Germany . |
| 0175165 | 10/1982 | Japan .................................... 514/356 |
| WO84/02132 | 6/1984 | PCT Int'l Appl. ................. 546/321 |

Primary Examiner—Sam Rosen
Attorney, Agent, or Firm—Finnegan, Henderson, Farabow, Garrett & Dunner

[57] ABSTRACT

Dihydropyridine derivatives and salts thereof represented by the general formula,

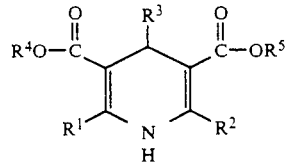

which possess excellent calcium antagonist effect, hypotensive effect, platelets aggregation inhibitory effect, phosphodiesterase inhibitory effect, calmodulin inhibitory effect and peroxidized lipid lowering effect, and thus dihydropyridine derivatives and salts thereof are useful as a coronary blood flow improving agent such as coronary vasodilator, hypotensive agent, prophylaxis and treating agents for thrombosis, phophodiesterase inhibitory agent, peroxidized lipid metabolism lowering agent, anti-inflammatory agent and others.

7 Claims, No Drawings

DIHYDROPYRIDINE DERIVATIVES

This application is a continuation of application Ser. No. 677,364, filed Nov. 30, 1984, now abandoned.

FIELD OF THE INVENTION

The present invention relates to dihydropyridine derivatives and salts thereof. More particularly, the present invention relates to dihydropyridine derivatives and salts thereof, process for preparing the same, as well as pharmaceutical composition containing the same as the active ingredient.

The dihydropyridine derivatives and salts thereof are novel compounds, and are not known in any of prior art references. The dihydropyridine derivatives and salts thereof according to the present invention are represented by the general formula (1),

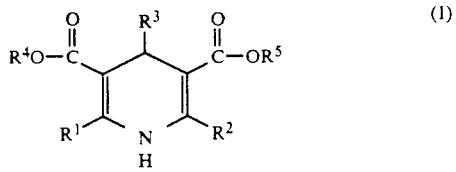

wherein $R^1$ and $R^4$ are each a lower alkyl group; $R^2$ is a lower alkyl group or a group of the formula —CH$_2$—A—R$^6$ [wherein A is a straight-chain or branched-chain unsaturated group hydrocarbon group which may have an oxygen atom or a group of the formula

(wherein $R^7$ is a lower alkyl group); and $R^6$ is a phenyl group which may have a hydroxyl group]; $R^3$ is a phenyl group which may have 1 to 2 substituents selected from the group consisting of a nitro group, a lower alkyl group which may have 1 to 3 halogen atoms, a lower alkoxy group and a halogen atom; and $R^5$ is a lower alkyl group, a 1,2,3,6-tetrahydropyridyl-lower alkyl group which may have, as the substituent, a phenyl group which may have halogen atoms or lower alkyl groups as the substituents on the phenyl ring, or a group of the formula —CH$_2$—A'—R$^8$ [wherein A' is a straight-chain or branched-chain unsaturated hydrocarbon group which may have or may not have an oxygen atom, a sulfur atom, a group of the formula

(wherein $R^7$ is a lower alkyl group) or a group of the formula

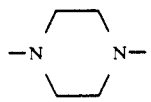

in the unsaturated hydrocarbon group; and $R^8$ is a phenyl group which may have 1 to 3 substituents selected from the group consisting of a lower alkoxy group, a halogen atom, a lower alkylthio group, a hydroxyl group, a lower alkanoyloxy group, a tetrahydropyranyloxy group and a lower alkoxy-lower alkoxy group; a pyridyl group; a thienyl group; furyl group, or a tetrazolyl group which may have a lower alkyl group as the substituent]; provided that when $R^5$ is a lower alkyl group, then $R^2$ should be a group of the formula —CH$_2$—A—R$^6$ (wherein A and $R^6$ are the same as defined above).

Dihydropyridine derivatives and salts thereof represented by the general formula (1) possess excellent calcium antagonist effect, hypotensive effect, platelets aggregation inhibitory effect, phosphodiesterase inhibitory effect, calmodulin inhibitory effect and peroxidized lipid lowering effect, and thus the dihydropyridine derivative and salt thereof represented by the general formula (1) are useful as a coronary blood flow improving agent such as coronary vasodilator, hypotensive agent, prophylaxis and treating agents for thrombosis, phosphodiesterase inhibitory agent, peroxidized lipid metabolism lowering agent, anti-inflammatory agent and others.

DESCRIPTION OF THE PRIOR ART

Compounds similar to the dihydropyridine derivatives according to the present invention are known from the disclosures in Japanese Patent Application Kokai (Laid-open) No. 51-108075 (1976) and Japanese Patent Application Kokai (Laid-open) No. 56-36455 (1981). Compounds of these prior art references are known as useful hypotensive agents, peripheral and cerebral vasodilating agents and treating agent for coronary blood vessels. On the contrary, dihydropyridine derivatives according to the present invention have features in that they perform their pharmacological effects for longer period of time with less side-effects as compared with known compounds. Furthermore, dihydropyridine derivatives according to the present invention are useful as carcinostatic agents.

SUMMARY OF THE INVENTION

An object of the present invention is to provide novel dihydropyridine derivatives.

Another object of the present invention is to provide process for preparing said dihydropyridine derivatives.

Further object of the present invention is to provide a pharmaceutical composition containing said dihydropyridine derivative as the active ingredient.

These and other objects and features of the present invention will become more fully apparent from the following description.

DETAILED DESCRIPTION OF PREFERRED EMBODIMENTS

Dihydropyridine derivatives represented by the general formula (1) according to the present invention, examples of various substituents as defined in $R^1$, $R^2$, $R^3$, $R^4$, $R^5$, $R^6$, $R^7$, $R^8$, A and A' are as follows.

As to the lower alkyl group, an alkyl group having 1 to 6 carbon atoms such as methyl, ethyl, propyl, isopropyl, butyl, tert-butyl, pentyl, hexyl groups and others can be exemplified.

As to the lower alkyl group which may have halogen atoms as the substituents, an alkyl group having 1 to 6 carbon atoms which may have 1 to 3 halogen atoms as the substituents, in addition to the above-mentioned alkyl groups having 1 to 6 carbon atoms, trifluoromethyl, 2,2-difluoroethyl, 1,1-dichloroethyl, trichloromethyl, dichloromethyl, tribromomethyl, 2,2,2-trifluoroethyl, 2,2,2-trichloroethyl, 2-chloroethyl, 1,2-dichloroethyl, 3,3,3-trichloropropyl, 3-fluoropropyl, 4-chlorobutyl, 3-chloro-2-methylethyl groups and others can be exemplified.

As to the lower alkoxy group, an alkoxy group having 1 to 6 carbon atoms such as methoxy, ethoxy, propoxy, isopropoxy, butoxy, tert-butoxy, pentyloxy, hexyloxy groups and others can be exemplified.

As to the halogen atom, fluorine atom, chlorine atom, bromine atom and iodine atom can be exemplified.

As to the lower alkoxy-lowered alkoxy group, an alkoxyalkoxy group of which the alkoxy moieties having 1 to 6 carbon atoms such as methoxymethoxy, 2-methoxyethoxy, 1-methoxyethoxy, 3-methoxypropoxy, 4-methoxybutoxy, 1,1-dimethyl-2-methoxyethoxy, 5-methoxypentyloxy, 6-methoxyhexyloxy, 2-methyl-3-methoxypropoxy, ethoxymethoxy, 3-ethoxypropoxy, 6-ethoxyhexyloxy, 2-propoxyethoxy, 4-propoxybutoxy, 5-butoxypentyloxy, pentyloxymethoxy, 1-pentyloxyethoxy, 1,1-dimethyl-2-hexyloxyethoxy, 3-hexyloxypropoxy groups and others can be exemplified.

As to the lower alkylthio group, an alkylthio group having 1 to 6 carbon atoms, such as methylthio, ethylthio, propylthio, isopropylthio, butylthio, tert-butylthio, pentylthio, hexylthio groups and others can be exemplified.

As to the lower alkanoyloxy group, an alkanoyloxy group having 1 to 6 carbon atoms, such as formyloxy, acetyloxy, propionyloxy, butyryloxy isobutyryloxy, pentanoyloxy, tert- butyryloxy, hexanoyloxy groups and others can be exemplified.

As to the phenyl group which may have 1 to 3 substituents selected from the group consisting of a lower alkoxy group, a halogen atom, a lower alkylthio group, a hydroxyl group, a lower alkanoyloxy group, a tetrahydropyranyloxy group and a lower alkoxy-lower alkoxy group, a phenyl group which may have 1 to 3 substituents selected from the group consisting of an alkoxy group having 1 to 6 carbon atoms, a halogen atom, an alkylthio group having 1 to 6 carbon atoms, a hydroxyl group, an alkanoyloxy group having 1 to 6 carbon atoms, a tetrahydropyranyloxy group and an alkoxyalkoxy group of which alkoxy moieties having 1 to 6 carbon atoms, such as phenyl, 2-, 3- or 4-chlorophenyl, 2-, 3- or 4-fluorophenyl, 2-, 3- or 4-bromophenyl, 2-, 3- or 4-iodophenyl, 3,5-dichlorophenyl, 2,6-dichlorophenyl, 3,4-dichlorophenyl, 3,4-difluorophenyl, 3,5-dibromophenyl, 2-, 3- or 4-methylthiophenyl, 2-, 3- or 4-ethylthiophenyl, 4-propylthiophenyl, 3-isopropylthiophenyl, 2-butylthiophenyl, 4hexylthiophenyl, 3-pentylthiophenyl, 4-tert-butylthiophenyl, 3,4-dimethylthiophenyl, 2,5-dimethylthiophenyl, 2-, 3- or 4-methoxyphenyl, 2-, 3- or 4-ethoxyphenyl, 3-propoxyphenyl, 4-isopropoxyphenyl, 3-butoxyphenyl, 2-pentyloxyphenyl, 4-tert-butoxyphenyl, 4-hexyloxyphenyl, 3,4-dimethoxyphenyl, 3,4-diethoxyphenyl, 2,5-dimethoxyphenyl, 2-, 3- or 4-(2-tetrahydropyranyloxy)phenyl, 2,4-bis(2-tetrahydropyranyloxy)phenyl 3-methylthio-4-chlorophenyl, 2-chloro-6-methylthiophenyl, 2-methoxy-3-hydroxyphenyl, 3,4,5-trimethoxyphenyl, 3,4,5-trimethylthiophenyl, 3,4,5-trichlorophenyl, 2-, 3- or 4-hydroxyphenyl, 3,4-dihydroxyphenyl, 2,6-dihydroxyphenyl, 3,4,5-trihydroxyphenyl, 2-, 3- or 4-acetyloxyphenyl, 4-propionyloxyphenyl, 3-isopropionyloxyphenyl, 2-butyryloxyphenyl, 4-hexanoyloxyphenyl, 3-pentanoyloxyphenyl, 4-tert-butyryloxyphenyl, 3,4-diacetyloxyphenyl, 2,5-diacetyloxyphenyl, 3,4,5-tridiacetyloxyphenyl, 2-methoxymethoxyphenyl, 3-(2-methoxyethoxy)phenyl, 4-(1-methoxyethoxy)phenyl, 2-(3-methoxypropoxy)phenyl, 3-(4-methoxybutoxy)-phenyl, 4-(1,1-dimethyl-2-methoxyethoxy)phenyl, 2-(5-methoxypentyloxy)phenyl, 3-(6-methoxyhexyloxy)phenyl, 4-(2-methyl-3-methoxypropoxy)phenyl, 2-(ethoxymethoxy)phenyl, 3-(3-ethoxypropoxy)phenyl, 4-(6-ethoxyhexyloxy)phenyl, 2-(2-propoxyethoxy)phenyl, 3-(4-propoxybutoxy)phenyl, 4-(5-butoxypentyloxy)phenyl, 2-(pentyloxymethoxy)phenyl, 3-(1-pentyloxyethoxy)phenyl, 4-(1,1-dimethyl-2-hexyloxyethoxy)-phenyl, 2-(3-hexyloxypropoxy)phenyl, 2-(3-hexyloxypropoxy)phenyl groups and others can be exemplified.

As to the phenyl group which may have 1 to 2 substituents selected from the group consisting of a nitro group, a lower alkyl group which may have 1 to 3 halogen atoms, a lower alkoxy group and a halogen atom, a phenyl group which may have 1 to 2 substituents, on the phenyl ring, selected from the group consisting of a nitro group, an alkyl group having 1 to 6 carbon atoms which may have 1 to 3 halogen atoms, an alkoxy group having 1 to 6 carbon atoms, and a halogen atom, such as a phenyl, 2-, 3- or 4-chlorophenyl, 2-, 3- or 4-fluorophenyl, 2-, 3- or 4-bromophenyl, 2-, 3- or 4-iodophenyl, 3,5-dichlorophenyl, 2,6-dichlorophenyl, 3,4-dichlorophenyl, 2,4-dichlorophenyl, 3,4-difluorophenyl, 3,5-dibromophenyl, 2-, 3- or 4-nitrophenyl, 2,4-dinitrophenyl, 2,6-dinitrophenyl, 3,4-dinitrophenyl, 3,5-dinitrophenyl, 2-, 3- or 4-methoxyphenyl, 2-, 3- or 4-ethoxyphenyl, 3-propoxyphenyl, 4-isopropoxyphenyl, 3-butoxyphenyl, 2-pentyloxyphenyl, 4-tert-butoxyphenyl, 4-hexyloxyphenyl, 3,4-dimethoxyphenyl, 3,4-diethoxyphenyl, 2,5-dimethoxyphenyl, 2-, 3- or 4-methylphenyl, 2-, 3- or 4-ethylphenyl, 4-propylphenyl, 3-isopropylphenyl, 2-butylphenyl, 4-hexylphenyl, 3-pentylphenyl, 4-tert-butylphenyl, 3,4-dimethylphenyl, 2,5-dimethylphenyl, 2-(trifluoromethyl)-phenyl, 3-(2,3-difluoroethyl)phenyl, 4-(1,1-dichloroethyl)-phenyl, 3-(trichloromethyl)phenyl, 2-(dichloromethyl)-phenyl, 4-(tribromomethyl)phenyl, 3-(2,2,2-trifluoroethyl)-phenyl, 2-(2-chloroethyl)phenyl, 4-(1,2-dichloroethyl)-phenyl, 3-(3,3,3-trichloropropyl)phenyl, 4-(3-chloro-2-methylethyl)phenyl, 3-(4-chlorobutyl)phenyl, 2-(3-fluoropropyl)phenyl, 3-methyl-4-chlorophenyl, 2-chloro-6-methylphenyl and 2-methoxy-3-nitrophenyl groups and others can be exemplified.

As to the 1,2,4,6-tetrahydropyridyl-lower alkyl group which may have, as the substituent, a phenyl group which may have halogen atoms or lower alkyl groups as the substituents on the phenyl ring, a 1,2,3,6-tetrahydropyridyl group substituted-alkyl group having 1 to 6 carbon atoms in the alkyl moiety, which may have as the substituent, a phenyl group which may have halogen atoms or alkyl groups having 1 to 6 carbon atoms, as the substituents on the phenyl ring, such as 1,2,3,6-tetrahydropyridylmethyl, 2-(1,2,3,6-tetrahydropyridyl)ethyl, 1-(1,2,3,6-tetrahydropyridyl)ethyl, 3-(1,2,3,6-tetrahydropyridyl)propyl, 4-(1,2,3,6-tetrahydropyridyl)butyl, 1,1-dimethyl-2-(1,2,3,6-tetrahydropyridyl)ethyl, 5-(1,2,3,6-tetrahydropyridyl)pentyl, 6-(1,2,3,6-tetrahydropyridyl)hexyl, 2-methyl-3-(1,2,3,6-tetrahydropyridyl)-propyl, (4-phenyl-1,2,3,6-tetrahydropyridyl)methyl, 2-[4-(2-fluorophenyl)-1,2,3,6-tetrahydropyridyl]ethyl, 1-[4-(3-bromophenyl)-1,2,3,6-tetrahydropyridyl]ethyl, 3-[3-(4-chlorophenyl)-1,2,3,6-tetrahydropyridyl]propyl, [4-(4-chlorophenyl)-1,2,3,6-tetrahydropyridyl]methyl, [4-(4-methylphenyl)-1,2,3,6-tetrahydropyridyl]methyl, [4-(2-(2-ethylphenyl)-1,2,3,6-tetrahydropyridyl]methyl, 1,1-dimethyl-2-[3-(3-propylphenyl)-1,2,3,6-tetrahydropyridyl]ethyl, 5-[2-(2-tert-butylphenyl)-1,2,3,6-tetrahydropyridyl]pentyl, 6-[3-(4-pentylphenyl)-1,2,3,6-tetrahydropyridyl]hexyl, and 2-methyl-3-[4-(3-hexylphenyl)-1,2,3,6-tetrahydropyridyl]propyl groups and others can be exemplified.

As to the straight-chain or branched-chain unsaturated hydrocarbon residual group which may have or may not have an oxygen atom, a sulfur atom, a group of the formula —N—R⁷ (wherein R⁷ is a lower alkyl group) or a group of the formula

in the unsaturated hydrocarbon residual group, a straight-chain or branched-chain unsaturated hydrocarbon residual group having 2 to 6 carbon atoms in the unsaturated hydrocarbon residual moiety, having 1 to 3 double bonds and/or triple bonds therein, said unsaturated hydrocarbon residual group may have or may not have an oxygen atom, a sulfur atom, a group of the formula

(wherein R⁷ is an alkyl group having 1 to 6 carbon atoms), or a group of the formula

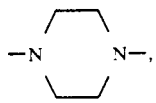

such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ylene, 2-hexenylene, 1-hexenylene, 5-hexenylene, 3-hexenylene, 4-hexenylene, 3,3-dimethyl-1-propenylene, 2-ethyl-1-propenylene, ethynylene, 2-propynylene, 1-propynylene, 1,1-dimethyl-2-propynylene, 3,3-dimethyl-1-propynylene, 2-butynylene, 3-buttnylene, 1-butynylene, 2-pentynylene, 1-pentynylene, 3-pentynylene, 4-pentynylene, 2-hexynylene, 1-hexynylene, 3-hexynylene, 4-hexynylene, 5-hexynylene, 1,3-hexadienylene, 1,4-hexadienylene, 1,3,5-hexatrienylene, 1-propenyleneoxy, 1-methyl-1-propenyleneoxy, 2-methyl-1-propenyleneoxy, 2-propenyleneoxy, 2-butenyleneoxy, 1-propenyleneoxymethylene, 1-butenyleneoxy, 3-butenyleneoxy, 2-pentenyleneoxy, 1-pentenyleneoxy, 3-pentenyleneoxy, 4-pentenyleneoxy, 1,3-butadienyleneoxy, 1,3-pentadienyleneoxy, 2-penten-4-yleneoxy, 2-hexenyleneoxy, 1-hexenyleneoxy, 5-hexenyleneoxy, 3-hexenyleneoxy, 4-hexenyleneoxy, 3,3-dimethyl-1-propenyleneoxy, 2-ethyl-1-propenyleneoxy, ethynyleneoxy, 2-propynyleneoxy, 1-propynyleneoxy, 1,1-dimethyl-2-propynyleneoxy, 3,3-dimethyl-1-propynyleneoxy, 3-butynyleneoxy, 1-butynyleneoxy, 2-pentynyleneoxy, 1-pentynyleneoxy, 3-pentynyleneoxy, 4-pentynyleneoxy, 2-hexynyleneoxy, 1-hexynyleneoxy, 3-hexynyleneoxy, 4-hexynyleneoxy, 5-hexynyleneoxy, 1,3-hexadienyleneoxy, 1,4-hexadienyleneoxy, 1,3,5-hexatrienyleneoxy, 1-propenyleneoxyethylene, 1-propenyleneoxypropylene, 1-methyl-1-propenyleneoxymethylene, 2-methyl-1-propenyleneoxyethylene, 2-propenyleneoxypropylene, 2-butenyleneoxymethylene, 1-butenyleneoxyethylene, 2-pentenyleneoxymethylene, 1,3-butadienyleneoxymethylene, 1,3-pentadienyleneoxymethylene, 1-propynyleneoxymethylene, 2-propynyleneoxyethylene, ethynyleneoxymethylene, 3-butynyleneoxymethylene, 1-butynyleneoxyethylene, 1-pentynyleneoxymethylene, 3,3-dimethyl-1-propynyleneoxymethylene, 1-propenylenethio, 1-methyl-1-propenylenethio, 2-methyl-1-propenylenethio, 2-propenylenethio, 2-butenylenethio, 1-propenylenethiomethylene, 1-butenylenethio, 3-butenylenetio, 2-pentenylenethio, 1-pentenylenethio, 3-pentenylenethio, 4-pentenylenethio, 1,3-butadienylenethio, 1,3-pentadienylenethio, 2-penten-4-ylenethio, 2-hexenylenethio, 1-hexenylenethio, 5-hexenylenethio, 3-hexenylenethio, 4-hexenylenethio, 3,3-dimethyl-1-propenylenethio, 2-ethyl-1-propenylenethio, ethynylenethio, 2-propynylenethio, 1-propynylenethio, 1,1-dimethyl-2-propynylenethio, 3,3-dimethyl-1-propynylenethio, 3-butynylenethio, 1-butynylenethio, 2-pentynylenethio, 1-pentynylenethio, 3-pentynylenethio, 4-pentynylenethio, 2-hexynylenethio, 1-hexynylenethio, 3-hexynylenethio, 4-hexynylenethio, 5-hexynylenethio, 1,3-hexadienylenethio, 1,4-hexadienylenethio, 1,3,5-hexatrienylenethio, 1-propenylenethioethylene, 1-propenylenethiopropylene, 1-methyl-1-propenylenethiomethylene, 2-methyl-1-propenylenethioethylene, 2-propenylenethiopropylene, 2-butenylenethiomethylene, 1-butenylenethioethylene, 2-pentenylenethiomethylene, 1,3-butadienylenethiomethylene, 1,3-pentadienylenethiomethylene, 1-propynylenethiomethylene, 2-propynylelethioethylene, ethynylenethiomethylene, 3-butynylenethiomethylene, 1-butynylenethioethylene, 1-pentynylenethiomethylene, 3,3-dimethyl-1-propynylenethiomethylene, 3,3-dimethyl-1-propynylenethiomethylene, N-methyl-N-(1-propenylene)amino, N-ethyl-N-(1-methyl-1-propenylene)amino, N-propyl-N-(2-methyl-1-propenylene)amino, N-n-butyl-N-(2-propenylene)amino, N-pentyl-N-(2-butenylene)amino, N-methyl-N-(1-propenylene)aminomethylene, N-hexyl-N-(1-butenylene)amino, N-methyl-N-(3-butenylene)amino, N-ethyl-N-(2-pentenylene)amino, N-propyl-N-(1-pentenylene)-amino, N-tert-butyl-N-(3-pentenylene)amino, N-pentyl-N-(4-pentenylene)amino, N-hexyl-N-(1,3-butadienylene)amino, N-methyl-N-(1,3-pentadienylene)amino, N-ethyl-N-(2-penten-4-ylnylene)amino, N-propyl-N-(2-hexenylene)amino, N-n-butyl-N-(1-hexenylene)amino N-pentyl-N-(5-hexenylene)-amino, N-hexyl-N-(3-hexenylene)amino, N-methyl-N-(1-propynylene)amino, N-ethyl-N-(1,1-dimethyl-2propynylene)amino, N-propyl-N-(3,3-dimethyl-1-propynylene)-amino, N-tert-butyl-N-(3-butynylene)amino, N-pentyl-N-(1-butynylene)amino, N-hexyl-N-(2-pentynylene)amino, N-methyl-N-(1-pentynylene)amino, N-ethyl-N-(3-pentynylene)-amino, N-propyl-N-(4-pentynylene)amino, N-butyl-N-(2-hexynylene)amino, N-pentyl-N-(1-hexynylene)amino, N-hexyl-N-(3-hexynylene)amino, N-methyl-N-(4-hexynylene)amino, N-ethyl-N-(5-hexynylene)amino, N-propyl-N-(1,3-hexadienylene)amino, N-tert-butyl-N-(1,4-hexadienylene)-amino, N-pentyl-N-(1,3,5-hexatrienylene)amino, N-hexyl-N-(1-propenylene)aminoethylene, N-methyl-N-(1-propenylene)-aminopropylene, N-ethyl-N-(1-methyl-1-propylene)-aminomethylene, N-propyl-N-(2-methyl-1-propenylene)-aminoethylene, N-butyl-N-(2-propenylene)aminopropylene, N-pentyl-N-(2-butenylene)aminomethylene, N-hexyl-N-(1-butenylene)aminoethylene, N-methyl-N-(2-pentenylene)-aminomethylene, N-ethyl-N-(1,3-butadienylene)aminomethylene, N-propyl-N-(1,3-pentadienylene)aminomethylene, N-methyl-N-(1-propynylene)aminomethylene, N-butyl-N-(2-propynylene)aminoethylene, N-pentyl-N-ethynyleneaminomethylene, N-hexyl-N-(3-butynylene)aminomethylene, N-methyl-N-(1-butynylene)aminoethylene, N-ethyl-N-(1-pentynylene)aminomethylene, N-methyl-N-(3,3-dimethyl-1-propynylene)aminomethylene, 4-(1-propenylene)-1-piperazinyl, 4-(1-methyl-1-propenylene)-1-piperazinyl, 4-(2-methyl-1-propenylene)-1-piperazinyl, 4-(2-propenylene)1-piperazinyl, 4-(2-butenylene)-1-piperazinyl, 4-(1-propenylene)-1-piperazinylmethylene, 4-(1-butenylene)-1-piperazinyl, 4-(3-butenylene)-1-piperazinyl, 4-(2-pentenylene)-1-piperazinyl, 4-(1-pentenylene)-1-piperazinyl, 4-(3-pentenylene)-1-piperazinyl, 4-(4-pentenylene)-1-piperazinyl, 4-(1,3-butadienylene)-1-piperazinyl, 4-(1,3-pentadienylene)-1-piperazinyl, 4-(2-penten-4-ynylene)-1-piperazinyl, 4-(2-hexenylene)-1-piperazinyl, 4-(1-hexenylene)-1-piperazinyl, 4-(5-hexenylene)-1-piperazinyl, 4-(1-butynylene)-1-piperazinylethylene, 4-(1-pentynylene)-1-piperazinylmethylene, 4-(3,3-dimethyl-1-propynylene)-1-piperazinylmethylene, 4-(3-hexenylene)-1-piperazinyl, 4-(4-hexenylene)-1-piperazinyl, 4-(3,3-dimethyl-1-propenylene)-1-piperazinyl, 4-(2-ethyl-1-propenylene)-1-piperazinyl, 4-(ethynylene)-1-piperazinyl, 4-(2-propynylene)-1-piperazinyl, 4-(1-propynylene)-1-piperazinyl, 4-(1,1-dimethyl-2-propynylene)-1-piperazinyl, 4-(3,3-dimethyl-1-propynylene)-1-piperazinyl, 4-(3-butynylene)-1-piperazinyl, 4-(1-butynylene)-1-piperazinyl, 4-(2-pentynylene)-1-piperazinyl, 4-(1-pentynylene)-1-piperazinyl, 4-(3-pentylene)-1-piperazinyl, 4-(4-pentynylene)-1-piperazinyl, 4-(2-hexynylene)-1-piperazinyl, 4-(1-hexynylene)-1-piperazinyl, 4-(3-hexynylene)-1-piperazinyl, 4-(4-hexynylene)-1-piperazinyl, 4-(5-hexynylene)-1-piperazinyl, 4-(1,3-hexadienylene)-1-piperazinyl, 4(1,4-hexadienylene)-1-piperazinyl, 4-(1,3,5-hexatrienylene)-1-piperazinyl, 4-(1-propenylene)-1-piperazinylethylene, 4-(1-propenylene)-1-piperazinylpropylene, 4-(1-methyl-1-propenylene)- 1-piperazinylmethylene, 4-(2-methyl-1-propenylene)-1-piperazinylethylene, 4-(2-propenylene)-1-piperazinylpropylene, 4-(2-butenylene)-1-piperazinylmethylene, 4-(1-butenylene)-1-piperazinylethylene, 4-(2-pentenylene)-1-piperazinylmethylene, 4-(1,3-butadienylene)-1-piperazinylmethylene, 4-(1,3-pentadienylene)-1-piperazinylmethylene, 4-(1-propynylene)-1-piperazinylmethylene, 4-(2-propynylene)-1-piperazinylethylene, 4-ethylene-1-piperazinylmethylene and 4-(3-butynylene)-1-piperazinylmethylene groups and others can be exemplified.

As to the tetrazolyl group which may have a lower alkyl group as the substituent, a tetrazolyl group which may have an alkyl group having 1 to 6 carbon atom as the substituent, such as tetrazolyl, 1-methyl-5-tetrazolyl, 1-ethyl-5-tetrazolyl, 1-propyl-5-tetrazolyl, 1-tert-butyl-5-tetrazolyl, 1-pentyl-5-tetrazolyl, 1-hexyl-5-tetrazolyl, 5-methyl-1-tetrazolyl, 5-isopropyl-1-tetrazolyl, 5-n-butyl-1-tetrazolyl, and 5-hexyl-1-tetrazolyl groups and others can be exemplified.

As to the phenyl group which may have a hydroxyl group as the substituent, phenyl, 2-, 3- or 4-hydroxyphenyl group can be exemplified.

As to the straight-chain or branched-chain unsaturated hydrocarbon group which may have or may not have an oxygen atom or a group of the formula

(wherein $R^7$ is a lower alkyl group), a straight-chain or branched-chain unsaturated hydrocarbon residual group having 2 to 6 carbon atoms in the unsaturated hydrocarbon residual moiety, having 1 to 3 double bonds and/or triple bonds therein, said unsaturated hydrocarbon residual group may have or may not have an oxygen atom or a group of the formula

(wherein $R^7$ is an alkyl group having 1 to 6 carbon atoms), such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, ethynylene, 2-propynylene, 1-propynylene, 1,1-dimethyl-2-propynylene, 3,3-dimethyl-1-propynylene, 2-butynylene, 3-butynylene, 1-butynylene, 2-pentynylene, 1-pentynylene, 3-pentynylene, 4-pentynylene, 2-hexynylene, 1-hexynylene, 3-hexynylene, 4-hexynylene, 5-hexynylene, 1,3-hexadienylene, 1,4-hexadienylene, 1,3,5-hexatrienylene, 1-propenyleneoxy, 1-methyl-1-propenyleneoxy, 2-methyl-1-propenyleneoxy, 2-propenyleneoxy, 2-butenyleneoxy, 1-propenyleneoxy methylene, 1-butenyleneoxy, 3-butenyleneoxy, 2-pentenyleneoxy, 1-pentenyleneoxy, 3-pentenyleneoxy, 4-pentenyleneoxy, 1,3-butadienyleneoxy, 1,3-pentadienyleneoxy, 2-penten-4-ynyleneoxy, 2-hexenyleneoxy, 1-hexenyleneoxy, 5-hexenyleneoxy, 3-hexenyleneoxy, 4-hexenyleneoxy, 3,3-dimethyl-1-propenyleneoxy, 2-ethyl-1-propenyleneoxy, ethynyleneoxy, 2-propynyleneoxy, 1-propynyleneoxy, 1,1-dimethyl- 2-propynyleneoxy, 3,3-dimethyl-1-propynyleneoxy, 3-butynyleneoxy, 1-butynyleneoxy, 2-pentynyleneoxy, 1-pentynyleneoxy, 3-pentynyleneoxy, 4-pentynyleneoxy, 2-hexynyleneoxy, 1-hexynyleneoxy, 3-hexynyleneoxy, 4-hexynyleneoxy, 5-hexynyleneoxy, 1,3-hexadienyleneoxy, 1,4-hexadienyleneoxy, 1,3,5-hexatrienyleneoxy, 1-propenyleneoxyethylene, 1-propenyleneoxypropylene, 1-methyl-1-propenyleneoxymethylene, 2-methyl-1-propenyleneoxyethylene, 2-propenylenexoypropylene, 2-butenyleneoxymethylene, 1-butenyleneoxyethylene, 2-pentenyleneoxymethylene, 1,3-butadienyleneoxymethylene, 1,3-pentadienyleneoxymethylene, 1-propynyleneoxymethylene, 2-propynyleneoxyethylene, ethynyleneoxymethylene, 3-butynyleneoxymethylene, 1-butynyleneoxyethylene, 1-pentynyleneoxymethylene, 3,3-dimethyl-1-propynyleneoxymethylene, N-methyl-N-(1-propenylene)amino, N-ethyl-N-(1-methyl-1-propenylene)amino, N-propyl-N-(2-methyl-1- propenylene)-amino, N-n-butyl-N-(2-propenylene)amino, N-pentyl-N-(2-butenylene)amino, N-methyl-N-(1-propenylene)aminomethylene, N-hexyl-N-(1-butenylene)amino, N-methyl-N-(3-butenylene)amino, N-ethyl-N-(2-tentenylene)amino, N-propyl-N-(1-pentenylene)amino, N-tert-butyl-N-(3-pentenylene)amino, N-pentyl-N-(4-pentenylene)amino, N-hexyl-N-(1,3-butadienylene)amino, N-methyl-N-(1,3-pentadienylene)amino, N-ethyl-N-(2-penten-4-ynylene)-amino, N-propyl-N-(2-hexenylene)amino, N-n-butyl-N-(1-hexenylene)amino, N-pentyl-N-(5-hexenylene)amino, N-hexyl-N-(3-hexenylene)amino, N-methyl-N-(1-propynylene)-amino, N-ethyl-N-(1,1-dimethyl-2-propynylene)amino, N-propyl-N-(3,3-dimethyl-1-propynylene)amino, N-tert-butyl-N-(3-butynylene)amino, N-pentyl-N-(1-butynylene)-amino, N-hexyl-N-(2-pentynylene)amino, N-ethyl-N-(3-pentynylene)amino, N-methyl-N-(1-pentynylene)amino, N-propyl-N-(4-pentynylene)amino, N-butyl-N-(2-hexynylene)-amino, N-pentyl-N-(1-hexynylene)amino, N-hexyl-N-(3-hexynylene)amino, N-methyl-N-(4-hexynylene)amino, N-ethyl-N-(5-hexynylene)amino, N-propyl-N-(1,3-hexadienylene)-amino, N-tert-butyl-N-(1,4-hexadienylene)amino, N-pentyl-N-(1,3,5-hexatrienylene)amino, N-hexyl-N-(1-propenylene)aminoethylene, N-methyl-N-(1 -propenylene)-aminopropylene, N-ethyl-N-(1-methyl-1-propenylene)-aminomethylene, N-propyl-N-(2-methyl-1-propenylene)-aminoethylene, N-butyl-N-(2-propenylene)aminopropylene, N-pentyl-N-(2-butenylene)aminomethylene, N-hexyl-N-(1-butenylene)aminoethylene, N-methyl-N-(2-pentenylene)-aminomethylene, N-ethyl-N-(1,3-butadienylene)aminomethylene, N-propyl-N-(1,3-pentadienylene)aminomethylene, N-methyl-N-(1-propynylene)aminomethylene, N-butyl-N-(2-propynylene)-aminoethylene, N-pentyl-N-ethynyleneaminomethylene, N-hexyl-N-(3-butynylene)aminomethylene, N-methyl-N-(1-butynylene)aminoethylene, N-ethyl-N-(1-pentynylene)-aminomethylene and N-methyl-N-(3,3-dimethyl-1-propynylene)aminomethylene groups and others can be exemplified.

Dihydropyridine derivatives and salts thereof represented by the general formula (1) according to the present invention can be prepared by various methods, for examples the derivatives can be prepared by the following Reaction process formula-1.

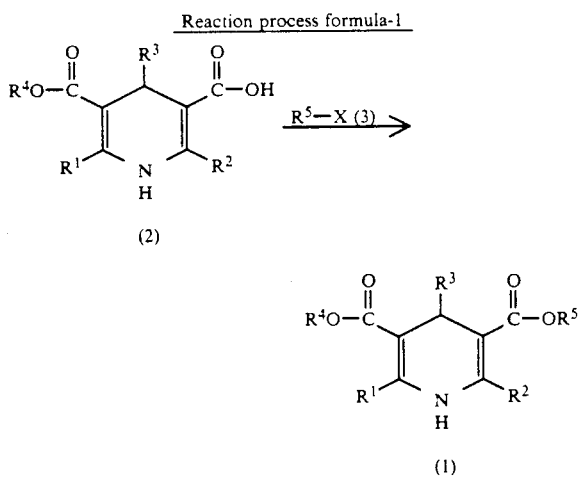

(wherein X is a hydroxyl group or a halogen atom; and $R^1$, $R^2$, $R^3$, $R^4$ and $R^5$ are the same as defined above).

In the reaction of compound (2) with compound (3), when X is a hydroxyl group, reaction conditions usually employed in esterification reaction can be used. The reaction may be conducted generally in the presence of a catalyst which is usually used in esterification reactions. As to the typical catalysts, there can be exemplified inorganic acids, such as hydrogen chloride, concentrated sulfuric acid, phosphoric acid, polyphosphoric acids, boron trifluoride and perchloric acid and others; organic acids, such as trifluoroacetic acid, trifluoromethanesulfonic acid, naphthalenesulfonic acids, p-toluenesulfonic acid, benzenesulfonic acid and ethanesulfonic acid and others; and dehydrating agents, such as trifluoromethanesulfonic acid anhydride, thionyl chloride, tetramethylureaoxalyl chloride, acetone dimethyl acetal, dicyclohexylcarbodiimide (DCC), 1-alkyl-2-halogenopyridinium halide or tosylate, N,N-carbonyldiimidazol and others can be exemplified. Additionally, acidic ion-exchange resins can also be used as the catalysts. The amount of these catalysts is not restricted in the specific range, and they can be used in any amount usually used in common esterification reaction.

The reaction may be carried out in the absence or presence of a solvent. As to the solvent used in the reaction, any solvent usually used in common esterification reaction may effectively be used. Specifically, as to the solvents, aromatic hydrocarbons, for example benzene, toluene and xylene; halogenated hydrocarbons, for example dichloromethane, dichloroethane, chloroform, carbon tetrachloride and others; ethers, for example diethyl ether, tetrahydrofuran, dioxane, ethylene glycol monomethyl ether, pyridine and others, and mixed solvents thereof can be exemplified.

In the above-mentioned reaction, the ratio of the amount of compound (3) to the amount of compound (2) can be selected from a wide range, and the former is used in an equimolar quantity to 5 times the molar quantity, preferably, the equimolar quantity to 2 times the molar quantity to the latter.

In carrying out of the above-mentioned reaction, the yield of the objective product ca be increased by removing the water formed in the reaction from the reaction system by using a dehydrating agent, such as anhydrous calcium chloride, anhydrous copper sulfate, anhydrous calcium sulfate, phosphorus pentoxide or the like. The reaction temperature of the reaction may be selected optionally, and there is not any restriction to the temperature, generally, the reaction may be carried out in the range from about −20° to 200° C., preferably, from about 0° C. to 150° C. The reaction is completed, generally in about 10 minutes to 20 hours depend on the kind of the starting materials and the reaction condition.

In the above-mentioned reaction, when X is a halogen atom, the objective product can be obtained by carrying out the reaction under conditions of dehydrohalogenating reaction. The dehydrohalogenating reaction is carried out by using a basic compound as the dehydrohalogenating agent. As to the basic compound, any known basic compound can be used, for example inorganic basic compounds such as sodium hydroxide, potassium hydroxide, sodium carbonate, potassium carbonate, sodium hydrogen carbonate, potassium hydrogen carbonate, silver carbonate and others; alcoholates such as sodium methylate, sodium ethylate and others; organic basic compounds such as triethylamine, pyridine, N,N-dimethylaniline and others can be exemplified.

The dehydrohalogenating reaction can advantageously be carried out in the presence of a solvent, and any inert solvent which does not give any adverse effect to the reaction can be used. As to the solvents, alcohols, such as methanol, ethanol, propanol, butanol, ethylene glycol and others; ethers, such as dimethyl ether, tetrahydrofuran, dioxane, ethylene glycol dimethyl ether, diethylene glycol dimethyl ether, and others; ketones such as acetone, methyl ether ketone and others; aromatic hydrocarbons, such as benzene, toluene, xylene and others; esters, such as methyl acetate, ethyl acetate and others; aprotic polar solvents, such as N,N-dimethylformamide, dimethyl sulfoxide, hexamethylphosphoryl triamide and others can be exemplified. Said reaction can also be carried out in the presence of a metal iodide, such as sodium iodide, potassium iodide and others. The ratio of the amount of a compound (3) to the amount of a compound (2) is not specifically restricted and can be selected from a wide range, generally an equimolar quantity to 5 times the molar quantity, preferably an equimolar quantity to 2 times the molar quantity of the former is used to the latter. The reaction temperature is also not specifically restricted, and generally the reaction is carried out at a room temperature to 200° C., preferably at from a room temperature to 160° C. The reaction is preferably carried out in 1 to 30 hours. Thus, dihydropyridine derivatives represented by the general formula (1) can be prepared.

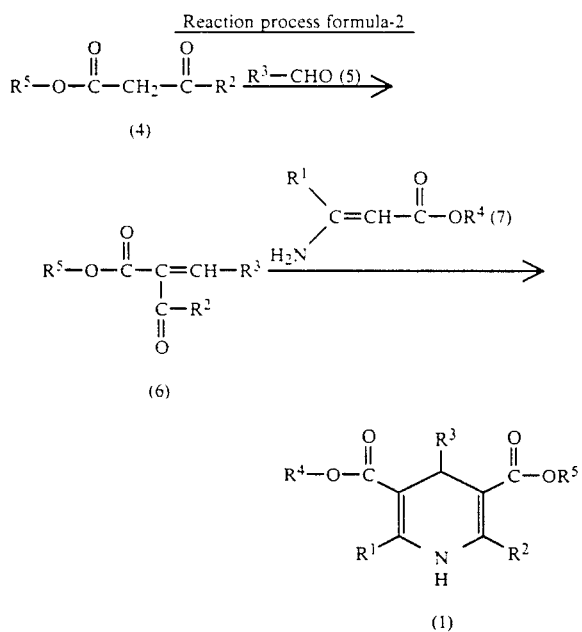

(wherein $R^1$, $R^2$, $R^3$, $R^4$ and $R^5$ are the same as defined above).

The reaction of compound (4) with compound (5) in the above-mentioned reaction process formula-2 can also be carried out in a suitable solvent in the presence or absence of a catalyst.

As to the solvent, alcohols, such as methanol, ethanol, propanol, isopropanol, butanol, ethylene glycol, and others; ethers, such as tetrahydrofuran, dioxane, ethylene glycol dimethyl ether, diethylene glycol dimethyl ether and others; aromatic hydrocarbons, such as benzene, toluene, xylene and others; halogenated hydrocarbons, such as methylene chloride, chloroform, 1,2-dichloromethane, and others; aprotic polar solvents, such as dimethyl sulfoxide, N,N-dimethylformamide, hexamethylphosphoryl triamide and others; carboxylic acids, such as acetic acid, propionic acid and others; and pyridine can be exemplified.

As to the catalyst used in the reaction, organic basic compounds, such as pyridine, piperidine, triethylamine, diethylamine, 1,8-diazabicyclo[5,4,0]undecene-5 (DBU) and others; metal alcoholates, such as sodium ethylate, sodium methylate and others, inorganic basic compounds, such as sodium hydroxide, potassium hydroxide, potassium carnoate, potassium acetate and others; mineral acids, such as hydrochloric acid, sulfuric acid and others; carboxylic acid, such as acetic acid, propionic acid and others, Lewis acids, such as boron trifluoride can be exemplified.

As to the ratio of the amount of compound (4) to the amount of compound (5), the latter may be used in an equimolar quantity, preferably an equimolar quantity to 2 times the molar quantity of the latter may be used to the former. As to the amount of the catalyst, 0.01 to 10 times the molar quantity, preferably, 0.1 to 5 times the molar quantity of the catalyst may be used to compound (4). The reaction may be carried out, generally at −20 to 200° C., preferably, −20 to 150° C., and the reaction is completed generally, in 10 minutes to 50 hours.

The reaction of compound (6) with compound (7) can advantageously by carried out in the presence of a solvent. As to the solvent, any inert solvent which does not give any adverse effect to the reaction can be used, for example, ketones, such as acetone; halogenated hydrocarbons such as chloroform and others; alcohols, such as methanol, ethanol, propanol, isopropanol, ethylene glycol and others; ethers, such as diethyl ether, tetrahydrofuran, dioxane, ethylene glycol dimethyl ether, diethylene glycol dimethyl ether and others; aromatic hydrocarbons, such as benzene, toluene, xylene and others; esters, such as methyl acetate, ethyl acetate and others; carboxylic acid, such as acetic acid, propionic acid and others; organic basic compounds such as pyridine and others; and aprotic polar solvent such as N,N-dimethylformamide, dimethyl sulfoxide, hexamethylphosphoryl triamide and others can be exemplified.

The ratio of the amount of compound (6) to the amount of compound (7) may be an equimolar quantity to 10 times the molar quantity, preferably an equimolar quantity to 2 times the molar quantity to the former. The reaction may generally be carried out at −20° to 200° C., preferably at 50° to 150° C. The reaction is generally completed in 10 minutes to 20 hours, then the desired compound represented by formula (1) can be obtained.

In conducting the reaction of compound (4) with compound (5) to form compound (6), then reacting compound (6) with compound (7) to prepare the desired compound (1), the intermediate compound (6) may not be separated from the reaction system, thus compound (5) and compound (7) may be existed within the same reaction system and make them reacted in a simultaneous (in one step) reaction.

Among the dihydropyridine derivatives represented by the general formula (1), those having, as for the symbol $R^8$, a phenyl group which contains at least one hydroxyl group as the substituent may be prepared by hydrolyzing a compound among those represented by the general formula (1) having, as for the symbol $R^8$, a phenyl group which contains at least one substituent selected from the group consisting of a lower alkoxy group, a tetrahydropyranyloxy group, a lower alkanoyloxy group and a lower alkoxy-lower alkoxy group.

The hydrolyzing reaction of the compound (1) [hereinafter referred to as "compound (1a)"] having, as for the symbol $R^8$, a phenyl group which contains at least one substituent selected from the group consisting of a lower alkoxy group, a tetrahydropyranyloxy group and a lower alkoxy-lower alkoxy group is carried out without in a solvent or with in a suitable solvent, by reacting an acid. As to the solvent used in this hydrolyzing reaction, water; nitrobenzene; aromatic hydrocarbons such as benzene, toluene, xylene and others; saturated, hydrocarbons such as hexane, octane and others; lower alcohols such as methanol, ethanol, isopropanol and others; ethers such as dioxane, tetrahydrofuran and others; ketones such as acetone and others; acetic acid; acetonitrile and mixed solvents thereof can be exemplified. As to the acid used in this hydrolyzing reaction, mineral acids such as hydrochloric acid, hydrobfomic acid, sulfuric acid and others; p-toluenesulfonic acid; pyridine p-toluenesulfonate; carboxylic acids such as acetic acid, propionic acid and others; aluminium chloride; tin chloride; boron trifluoride; zinc chloride and others can be exemplified. The amount of the acid to be used to the amount of compound (1a) may be at least an equimolar quantity, generally a large excess quantity may be used. The reaction may be carried out generally from $-30°$ to $200°$ C., preferably from $-30°$ to $100°$ C., and the reaction is generally completed in about 0.5 to 8 hours.

The hydrolyzing reaction of the compound (1) having, as for the symbol $R^8$, a phenyl group which contains at least one lower alkanoyloxy group, is carried out under reaction conditions widely employed in hydrolyzing reaction of esters. For example, the hydrolyzing reaction is carried out under conditions of in the presence of an acid or alkali catalyst, in an inert solvent at $0°$ to $100°$ C., for 1 to 5 hours. As to the catalyst, inorganic acids such as hydrochloric acid, sulfuric acid, aluminium chloride and others; organic acids such as acetic acid, formic acid and others; inorganic basic compounds such as sodium hydroxide sodium carbonate, potassium hydroxide and others; ammonia; organic basic compounds such as triethylamine and others can be exemplified. As to the inert solvent, water; alcohols such as methyl alcohol, ethyl alcohol and others; carboxylic acids such as acetic acid, propionic acid and others; ethers such as diethyl ether and others; amides such as dimethylformamide, acetamide and others can be exemplified.

Among the dihydropyridine derivatives represented by the general formula (1), those having, as for the symbol $R^8$, a phenyl group which contains at least one substituent selected from the group consisting of a lower alkoxy group, a tetrahydropyranyloxy group and a lower alkoxy-lower alkoxy group, can also be prepared by alkylating a compound hereinafter referred to as "compound (1b)" having, as for the symbol $R^8$, a phenyl group which contains at least one hydroxyl group as the substituent. Said alkylating reaction is carried out under conditions usually employed in common alkylating reaction. For example, alkylation is carried out by using an alkylating agent in the presence of a basic compound. As to the basic compound used in this reaction, alkali metals such as metallic sodium, metallic potassium and others; and the hydrides, hydroxides, carbonates, bicarbonates or alcoholates of these alkali metals; aromatic amines compounds such as pyridine, piperidine, and others; organic basic compounds such as triethylamine, N,N-diethylaniline, 1,8-diazabicyclo[5,4,0]undecene-7 (DBU) and others can be exemplified. As to the alkylating agent, a lower alkyl halide, a tetrahydropyranyl halide, dihydropyran, a lower alkoxy-lower alkyl halide, a dialkyl sulfate, a diazoalkane and others can be exemplified.

In using a lower alkyl halide, a tetrahydropyranyl halide or a lower alkoxy-lower alkoxy halide as the for alkylating agent, the alkylating reaction is carried out effectively in a suitable solvent. As to the solvent to be used, water; a lower alcohols such as methanol, ethanol, isopropanol, n-butanol and others; ethers such as diethyl ether, dioxane, tetrahydrofuran and others; ketones such as acetone, methyl ethyl ketone and others; halogenated hydrocarbons such as chloroform, dichloroethane and others; aromatic hydrocarbons such as nitrobenzene, chlorobenzene, benzene, toluene, xylene and others; aprotic polar solvents such as N,N-dimethylformamide, dimethyl sulfoxide and others can be exemplified. The amount of the alkylating agent to the amount of compound (1b), at least an equimolar quantity, preferably an equimolar quantity to 5 times the molar quantity may be used to the latter. The reaction is generally carried out at from $-20°$ to $200°$ C., preferably at $0°$ to $100°$ C., and is completed in about 10 minutes to 24 hours.

In using a dialkyl sulfate as for the alkylating agent, the alkylation reaction is carried out in an inert solvent at a room temperature to $150°$ C. As to the dialkyl sulfate, dimethyl sulfate, diethyl sulfate and others can be exemplified. As to the inert solvent, aromatic hydrocarbons such as benzene, toluene and others; ethers such as dioxane, tetrahydrofuran, diethyl ether and others can be exemplified.

In using dihydropyran as for the alkylating agent, the alkylating reaction is carried out in the presence of an acid, in a solvent, and generally at $0°$ to $150°$ C., preferably at $0°$ to about $100°$ C., and the reaction is completed in 0.5 to 10 hours. As to the acid to be used in this case, mineral acids such as hydrochloric acid, hydrobromic acid, sulfuric acid and others; p-toluenesulfonic acid; pyridine p-toluenesulfonate and others can be exemplified. As to the solvent, lower alcohols such as methanol, ethanol, isopropanol and others; ethers such as diethyl ether, dioxane, tetrahydrofuran and others; aromatic hydrocarbons such as benzene, toluene and others; saturated hydrocarbons such as hexane, octane and others; ketones such as acetone and; acetic acid; acetonitrile and mixtures of these solvents can be exemplified.

The amount of dihydropyran to the amount of compound (1b), generally an equimolar quantity, preferably an equimolar to 5 times the molar quantity of the former may be used to the latter.

Among the dihydropyridine derivatives represented by the general formula (1), those having, as for the symbol $R^8$, a phenyl group which contains at least one lower alkanoyloxy group as the substituent, can also be prepared by acylating a compound (1b). Said acylating reaction is carried out by using an acid halide such as a lower alkanoic acid halide, or an alkanoic acid anhydride under conventional method. The reaction by using acid halide is carried out in an inert solvent, and if necessary in the presence of a dehydrohalogenating agent such as an amine for example triethylamine, diisopropylethylamine, pyridine, N,N-diethylaniline and others, and at −50° to 150° C., in 1 to 24 hours. In carrying out the acylating reaction by using acid anhydride, the reaction is conducted in an inert solvent at a room temperature to 200° C., in 1 to 10 hours. As to the inert solvent used in the above-mentioned reaction, aromatic hydrocarbons such as nitrobenzene, chlorobenzene and others; amines such as pyridine, N,N-dimethylaniline and others; ethers such as diethyl ether, tetrahydrofuran and others; halogenated hydrocarbons such as dichloromethane, dichloroethane, chloroform and others can be exemplified. The amount of the acrylating agent used to the amount of compound (1b), generally at least an equimolar quantity, preferably an equimolar to 5 times the molar quantity of the former may be used to the latter.

Compounds represented by the general formula (3) as used for the starting material in the above-mentioned reaction process formula-1, and compounds represented by the general formula (4) as used for the starting material in the above-mentioned reaction process formula-2 contain novel compounds, said compounds represented by the general formulas (3a), (3b), (3c) and (3d) are prepared by the following reaction process formulas-3 to -5.

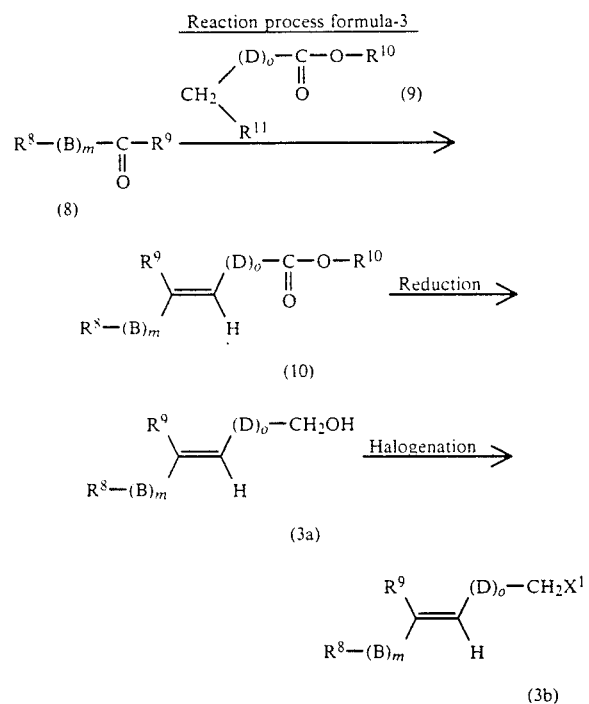

[wherein $R^8$ is the same as defined above; $R^9$ is a hydrogen atom or a lower alkyl group; $R^{10}$ is a lower alkyl group; $R^{11}$ is a carboxyl group or a group of the formula

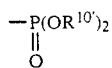

(wherein $R^{10'}$ is a lower alkyl group); B and D are each an unsaturated alkylene group; m and o are 0 and 1 respectively; $X^1$ is a halogen atom; provided that the carbon atom number in the group of the formula

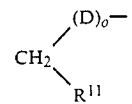

should not exceed 6].

The reaction of compound (8) with compound (9) can be carried out in the presence of a basic compound, in a solvent. As to the basic compound, inorganic basis such as metallic sodium, metallic potassium, sodium hydride, sodium amide, sodium hydroxide, potassium hydroxide, sodium carbonate, potassium carbonate, sodium hydrogen carbonate and others; metal alcoholates such as sodium methylate, sodium ethylate and others; organic basis compounds such as pyridine, piperidine, quinoline, triethylamine, N,N-dimethylaniline and others can be exemplified. As to the solvent, any inert solvent which does not give any adverse effect to the reaction can be used, for example, ethers such as diethyl ether, dioxane, tetrahydrofuran, ethylene glycol dimethyl ether, diethylene glycol dimethyl ether and others; aromatic hydrocarbons such as benzene, toluene, xylene and others; aliphatic hydrocarbons n-hexane, heptane, cyclohexane and others, amines such as pyridine, N,N-dimethylaniline and others; aprotic polar solvents such as N,N-dimethylformamide (DMF), dimethyl sulfoxide (DMSO), hexamethylphosphoryl triamide (HMPA) and others can be exemplified. The reaction is generally carried out at 0° to 150° C., preferably from a room temperature to about 120° C., and is generally completed in 0.5 to 15 hours. The amount of compound (8) to the amount of compound (9) is generally an equimolar quantity, preferably an equimolar quantity to 2 times the molar quantity of the latter is used to the former.

The reduction of compound (10) is generally carried out by using a hydrogenation reducing agent. As to the hydrogenation reducing agent, sodium borohydridem lithium aluminum hydride, aluminum dialkyl hydride such as aluminum diisobutyl hydride (DIBAL), diborane and others. The amount of the hydrogenation reducing agent to the amount of compound (10) is that generally 0.1 to 3 times the molar quantity, preferably 0.5 to 2 times the molar quantity of the former is used to the latter. The reaction is carried out generally in a suitable solvent, for example water; a lower alcohols such as methanol, ethanol, isopropanol and others; ethers such as tetrahydrofran, diethyl ether, diethylene glycol dimethyl ether and others; aromatic hydrocarbons such as benzene, toluene, xylene and others can be used, at −60° to 50° C., preferably at −40° C. to a room temperature, for about 10 minutes to 5 hours. In carrying out of the reaction by using lithium aluminum hydride, aluminum dialkyl hydride or diborane as for the reducing agent, an anhydrous solvent such as diethyl ether, tetrahydrofuran, diethylene glycol dimethyl ether, benzene, toluene or xylene may preferably be used.

The halogenation reaction of compound (3a) thus prepared is carried out in a solvent for example, an ether such as dioxane, tetrahydrofuran or the like; a chlorinated hydrocarbon such as chloroform, methylene chloride, carbon tetrachloride or the like, or without a solvent, by reacting a compound (3a) with a halogenating agent for example a hydrohalic acid such as hydrochloric acid or hydrobromic acid; N,N-diethyl-1,2,2-trichlorovinylamide, phosphorus pentachloride, phosphorus pentabromide, phosphorus oxychloride, thionyl chloride or the like, at a room temperature to 150° C., preferably at a room temperature to 80° C., for 1 to 6 hours. The amount of the halogenating agent to the amount of a compound (3a) is that at least an equimolar quantity, generally a large excess quantity of the halogenating agent may be used to the latter.

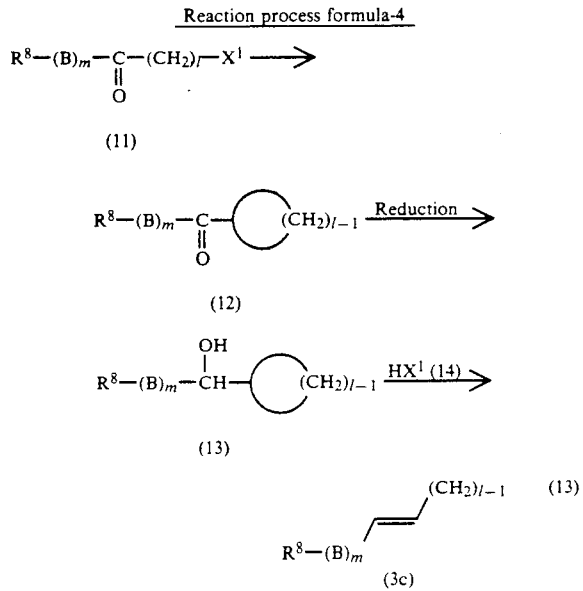

[wherein $R^8$, B, m and $X^1$ are the same as defined above; l is an integer of 3 to 6; provided that the number of carbon atoms in a group of the formula $-(B)_m-CH=CH-(CH_2)_{l-1}$ should not be over 6].

The reaction for preparing compound (12) from compound (11) is carried out in the presence of a basic compound, in an inert solvent for example, an ether such as dioxane, tetrahydrofuran, ethylene glycol dimethyl ether or the like; an aromatic hydrocarbon such as benzene, toluene, xylene or the like; a lower alcohol such as methanol, ethanol, isopropanol or the like; a polar solvent such as acetonitrile, N,N-dimethylformamide, dimethyl sulfoxide or the like. As to the basic compound, inorganic basic compounds such as calcium carbonate, sodium carbonate, potassium carbonate, sodium hydrogen carbonate, sodium hydroxide, potassium hydroxide, sodium amide, sodium hydride, potassium hydride, sodium methylate, sodium ethylate and others; and organic basic compounds such as triethylamine, pyridine, quinoline, 1,5-dibiazabicyclo[4,3,0]nonene-5 (DBN), 1,8-diazabicyclo-[5,4,0]undecene-7 (DBU), 1,4-diazabicyclo[2,2,2]octane (DABCO) and others can be exemplified. The reaction is generally carried out at a room temperature to 200° C., preferably at 60° to 120° C., and the reaction is generally completed in 1 to 24 hours.

Reduction reaction of a compound (12) is carried out under the same conditions similar to those employed in the reduction of a compound (10) in the above-mentioned reaction process formula-3.

The reaction of a compound (13) with a compound (14) is carried out in a suitable inert solvent. As to the solvent to be used in the reaction, ethers such as dioxane, tetrahydrofuran, diethyl ether and others; halogenated hydrocarbons such as chloroform, methylene chloride, carbon tetrachloride and others can be exemplified. The reaction temperature is generally at o to 150° C., preferably at 0° to about 100° C., and generally, the reaction is completed in 10 minutes to 6 hours. The amount of the compound (14) to the amount of the compound (13) is that generally at least an equimolar quantity, preferably in a large excess amount of the former is used to the latter.

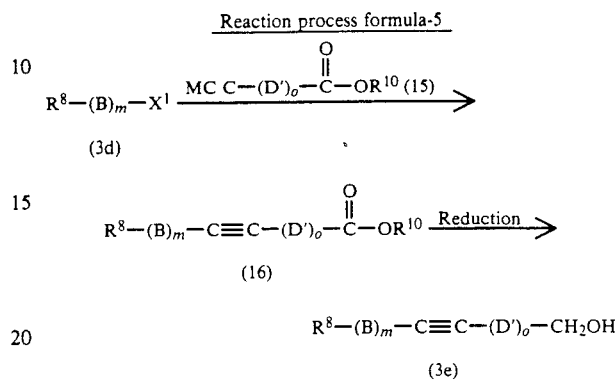

[wherein $R^8$, $R^{10}$, B, $X^1$, m and o are the same as defined above; M is a metal such as copper, sodium, lithium, potassium; D' is a saturated- or unsaturated-alkylene group; provided that the number of the carbon atoms in a group of the formula $-(B)_m-C\equiv C-(D')_o$ should not be exceed over 6].

The reaction of a compound (3d) with a compound (15) is carried out in a suitable solvent. As to the solvent used in the reaction, ethers such as diethyl ether, dioxane, tetrahydrofuran, ethylene glycol dimethyl ether, diethylene glycol dimethyl ether and others; aromatic hydrocarbon such as benzene, toluene, xylene; aliphatic hydrocarbons such as n-hexane, heptane, cyclohexane and others; amines such as triethylamine, pyridine, N,N-dimethylaniline and others; aprotic polar solvents such as N,N-dimethylformamide (DMF), dimethyl sulfoxide (DMSO), hexamethylphosphoryl triamide (HMPA) and others can be exemplified. The reaction temperature is generally 0° to 200° C., preferably from a room temperature to at about 150° C., and the reaction is generally completed in 0.5 to 10 hours. The amount of the compound (15) to the amount of the compound (3d) is that at least an equimolar quantity, preferably an equimolar to 1.5 times the molar quantity of the former is used to the latter.

The reduction reaction of a compound (16) can be carried out under the same conditions those employed in the reduction of a compound (10) in reaction process formula-3.

Compounds represented by the general formulas (3a), (3b), (3c) and (3d) can be converted into a compound represented by the general formula (17),

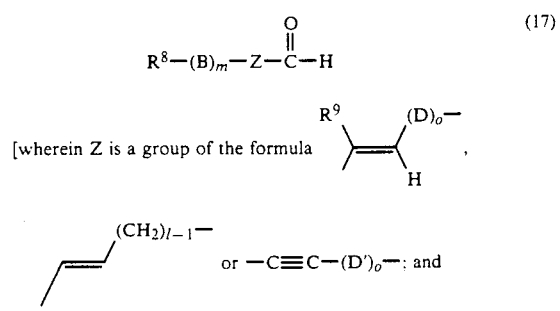

-continued

R$^8$, R$^9$, B, D, m, o and l are the same as defined above], by oxidizing in the presence of a suitable oxidizing agent.

A part of compounds represented by the general formula (17) correspond to compound (8) which is the starting material used in the above-mentioned reaction process formula-3, thus various desired compounds represented by the general formula (3) can be obtained by carrying out the reaction in sequently in the above-mentioned reaction process formula-3 to -5 and -9 and the above-mentioned oxidation reaction. As to the oxidizing agent used in the above-mentioned oxidation reaction, chromium compounds such as potassium chromate, sodium bichromate, chromium trioxide, pyridinium chlorochromate, anhydrous chromium trioxide-dipyridine complex and others; manganese compounds such as manganese dioxide, potassium permangante and others; lead tetraacetate; periodic acid; dimethyl sulfoxide; amine oxides such as dimethylamine oxide; pyridine-nitroso compounds such as pyridine-p-nitro-N,N-dimethylaniline and others can be exemplified. As to the solvent used to the reaction, aromatic hydrocarbons such as benzene, toluene, xylene and others; halogenated hydrocarbons such as methylene chloride, chloroform, carbon tetrachloride and others; ethers such as diethyl ether, dioxane, tetrahydrofuran and others, aliphatic hydrocarbons such as haxane, pentane, cyclohexane and others, ketones such as acetone, methyl ethyl keton and others; lower alcohols such as methanol, ethanol, isopropanol; water, acetic acid, dimethyl sulfoxide and others can be exemplified. The reaction can be carried out by using an acid such as sulfuric acid or perchloric acid as the catalyst. The reaction is carried out generally at 0° to 200° C., preferably at 0° to about 150° C., is completed generally in 0.5 to 15 hours.

A compound represented by the general formula (11) as used for the starting material in the above-mentioned reaction is prepared by for example the following reaction process formula-7.

Reaction process formula-7

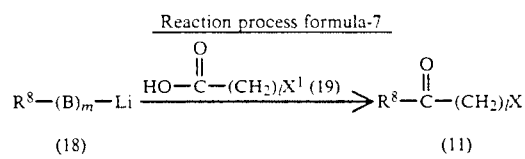

(18)          (11)

[wherein R$^8$, B, m, l and X$^1$ are the same as defined above].

The reaction of a compound (18) with a compound (19) is carried out in a suitable solvent. As to the solvent used in the reaction, ethers such as diethyl ether, dioxane, tetrahydrofuran, 1,2-dimethoxyethane and others; aromatic hydrocarbons such as benzene, toluene, xylene and others; aliphatic hydrocarbons such as hexane, heptane, pentane and others; and mixtures of these solvents and others can be exemplified.

The reaction is carried out generally at −70° to 50° C., preferably −65° C. to about a room temperature, and is generally completed in 3 to 30 hours. The amount of the compound (19) to the amount of the compound (18) is that at least 2 times the molar quantity, preferably 2 to 3 times the molar quantity of the former is used to the latter.

Among the compounds represented by the general formula (11), those in which the symbol m is 0 thus compound (11a) may be prepared by the following reaction process formula-8.

Reaction process formula-8

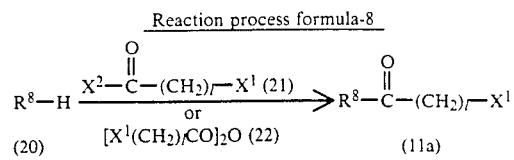

(20)          (22)          (11a)

(wherein R$^8$, X$^1$ and l are the same as defined above; and X$^2$ is a halogen atom).

The reaction of a compound (20) with a compound (21) or compound (22) is generally called as Friedel-Crafts reaction, and can be carried out in a suitable solvent in the presence of a Lewis acid. As to the solvent used in the reaction, any solvent generally used in this type of reaction can advantageously be employed, for example carbon disulfide, nitrobenzene, chlorobenzene, dichloroethane, dichloromethane, trichloroethane, tetrachloroethane and others can be exemplified. As to the Lewis acid used in this reaction, those used conventionally in this type of reaction can preferably be used, for example aluminum chloride, zinc chloride, iron chloride, tin chloride, boron trifluoride, boron tribromide, concentrated sulfuric acid and others can be used. The amount of Lewis acid may be determined suitably, and generally 2 to 6 times the molar quantity, preferably 3 to 4 times the molar quantity of a Lewis acid may be used to a compound (20). The amount of the compound (21) or compound (22) to the amount of the compound (20) is that generally at least an equimolar quantity, preferably an equimolar quantity to 3 times the molar quantity of the former is used to the latter. The reaction temperature can be selected from a wide range, and generally the reaction is carried out at 0° to 120° C., preferably from o° to 70° C., and the reaction is completed in 0.5 t about 6 hours.

Reaction process formula-9

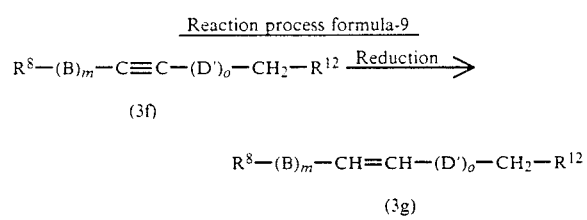

[wherein R$^8$, B, D', m and o are the same as defined above; R$^{12}$ is a hydroxyl group or a lower alkanoyl group; provided that the number of the carbon atoms in a group of the formula —(B)$_m$—C≡C—(D')$_o$—CH$_2$— and a group of the formula —(B)$_m$—CH≡CH—(D')$_o$—CH$_2$— should not exceed over 6.].

The reduction of a compound (3f) can be carried out by methods according to various reducing reactions known in the art. For example, catalytic reducing method by using palladium black, palladium carbon, platinum oxide, platinum black, Raney nickel, Lindlar catalyst and others as for the reducing catalysts; reducing methods by using sodium borohydride, lithium aluminum hydride and others as for the reducing agents can be employed.

In carrying out the catalytic reduction, the reaction can be conducted by using a conventional solvent for example water, methanol, ethanol, isopropanol, acetic acid, dioxane, tetrahydrofuran and others, and in the presence of the above-mentioned catalyst, under a normal atmospheric pressure to 20 atmospheric pressure, preferably, from a normal atmospheric pressure to 10 atmospheric pressure of hydrogen, and generally at −30° C. to 100° C., preferably 0° C. to 50° C. The amount of the catalyst is generally 0.1 to 40% by weight, preferably from 1 to 20% by weight of the catalyst is used to a compound (3f), and the reaction is generally completed in 1 to 12 hours.

In carrying out the reaction by using a reducing agent such as lithium aluminum hydride, an equimolar quantity to 20 times the molar quantity, preferably 1.5 to 3.5 times the molar quantity of the reducing agent is used to the compound (2f). The reduction reaction is carried out in a conventional solvent such as diethyl ether, tetrahydrofuran, dioxane or the like, and generally at −30° to 100° C., preferably at 0° C. to 70° C., and is completed in 30 minutes to about 12 hours. According to these procedures, a compound represented by the general formula (3g) can easily be obtained.

Among the compounds represented by the general formula (3g), those having a lower alkanoyloxy group as for the symbol $R^{12}$, can be converted into a compound (3g) having a hydroxy group as for the symbol $R^{12}$ under the conditions similar to those employed in the hydrolysis of a compound (1) wherein $R^8$ is a phenyl group which contains at least one lower alkanoyloxy group as the substituent.

A part of compounds represented by the general formula (3f) can be prepared by a method according to the following reaction process formula-10.

Reaction process formula-10

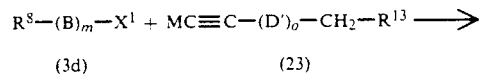

(3d)    (23)

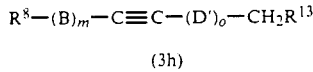

(3h)

[wherein $R^8$, B, m, $X^1$, M, D' and o are the same as defined above; $R^{13}$ is a hydroxyl group, tetrahydropyranyloxy group, a lower alkoxy-lower alkoxy group or a lower alkanoyl group; provided that the number of the carbon atoms in a group of the formula $-(B)_m-C\equiv C-(D')_o-CH_2-$ should not exceed over 6].

The reaction of a compound (3d) with a compound (23) can be carried out under the same reaction conditions employed in the reaction of a compound (3d) with a compound (15) in the above-mentioned reaction process formula-5.

Reaction process formula-11

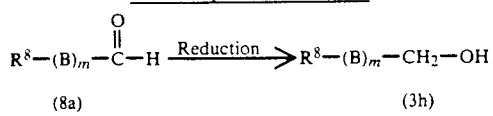

(8a)    (3h)

[wherein $R^8$, B, and m are the same as defined above].

The reduction reaction of a compound (8a) can be carried out under the same reaction conditions employed in the reduction of a compound (10) in the above-mentioned reaction process formula-3.

Reaction process formula-12

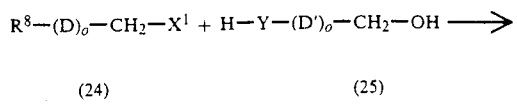

(24)    (25)

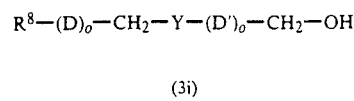

(3i)

[wherein $R^8$, D, D' and o are the same as defined above; Y is an oxygen atom, a sulfur atom, a group of the formula

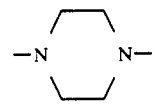

or a group of the formula

(wherein $R^7$ is the same as defined above); provided that the number of the carbon atoms in a group of the formula $-(D)_o-CH_2-Y-(D)'_o-CH_2-$ should not be exceeded over 6].

The reaction of a compound (24) with a compound (25) can be carried out in a suitable solvent or without solvent, in the absence or presence of a basic compound. As to the solvent used in the reaction, water; lower alcohols such as methanol, ethanol, isopropanol and others; halogenated hydrocarbons such as dichloromethane, dichloroethane, chloroform, carbon tetrachloride and others; ethers such as diethyl ether, tetrahydrofuran, dioxane and others; aliphatic hydrocarbons such as n-hexane octane, cyclohexane and others; aromatic hydrocarbons such as benzene, toluene, xylene and others; aprotic polar solvents such as acetone, acetonitrile, N,N-dimethylformamide, dimethyl sulfoxide, hexamethylphosphoryl triamide and others; and mixtures of these solvents can be exemplified. As to the solvent used in the reaction, inorganic basic compounds such as sodium hydroxide, potassium hydroxide, sodium carbonate, potassium carbonate, sodium hydrogen carbonate, potassium hydrogen carbonate, sodium amide, sodium hydride and others; alcoholates such as sodium methylate, sodium ethylate and others; organic basic compounds such as triethylamine, pyridine, N,N-dimethylaniline and others can be exemplified.

The said reaction can be advantageously proceed by using a charge-transfer catalyst such as tetrabutylammonium bromide and others. The reaction is carried out generally, at 0° to 150° C., preferably at 0° to 120° C., and is completed in about 1 to 10 hours. The ratio of the amount of a compound (24) to the amount of a compound (25) is that generally an equimolar quantity, preferably an equimolar quantity to 10 times the molar quantity of the former is used to the latter.

A compound (4) used as the starting material in the reaction process formula-2 can be prepared by methods according to reaction process formula-13 and -14 as follows.

Reaction process formula-13

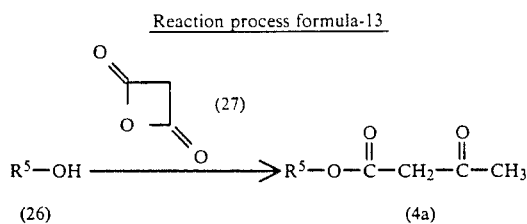

[wherein $R^5$ is the same as defined above].

The reaction of a compound (26) with a compound (27) in the above-mentioned reaction process formula-13 is carried out in a suitable solvent in the presence of a catalyst As to the catalyst, basic compounds for example, organic basic compounds such as triethylamine, pyridine, N,N-dimethylaniline and others; inorganic basic compounds such as sodium acetate, potassium carbonate; and acidic compounds for example, sulfonic acids such as p-toluenesulfonic acid and others; Lewis acids such as boron trifluoride and others can be exemplified. As to the solvents, aromatic hydrocarbons such as benzene, toluene, xylene and others; esters such as methyl acetate, ethyl acetate and others; halogenated hydrocarbons such as methylene chloride, chloroform, 1,2-dichloroethane and others; ethers such as diethyl ether, tetrahydrofuran, dioxane, ethylene glycol dimethyl ether, dithylene glycol dimethyl ether and others; ketones such as acetone, methyl ethyle ketone and others; aprotic polar solvents such as N,N-methylformamide, dimethyl sulfoxide, hexamethylphosphoryl trimaide, N-methylpyrrolidone and others can be exemplified. As to the ratio of the amount of the compound (26) to the amount of the compound (27), generally at least an equimolar quantity, preferably an equimolar quantity to 2 times the molar quantity of the latter may be used to the former. The amount of the catalyst is not specifically restricted, and generally 0.01 to 10 times the molar quantity, preferably 0.1 to 5 times the molar quantity of the catalyst may be used to the compound (26). The reaction is carried out generaly at $-20°$ to 200° C., preferably at $-20°$ to 100° C., and is completed in 10 minutes to 20 hours.

Reaction process formula-14

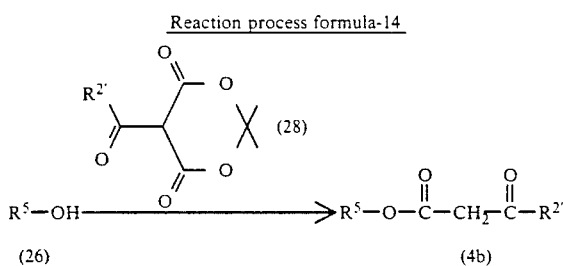

[wherein $R^5$ is the same as defined above; and $R^{2'}$ is a lower alkyl group].

The reaction of a compound (26) with a known compound (28) may be carried out under the same conditions employed in the reaction of a compound (26) with a compound (27) in the above-mentioned reaction process formula-13.

Reaction process formula-15

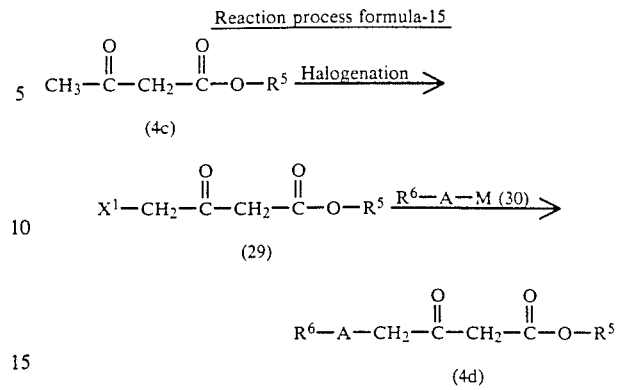

[wherein $R^5$, $X^1$, M, A and $R^6$ are the same as defined above].

The halogenation reaction of a compound (4c) can be carried out in a suitable solvent, in the presence of a halogenating agent. As to the solvent used in the halogenation reaction, halogenated hydrocarbons such as chloroform, dichloromethane, carbon tetrachloride and others; ethers such as diethyl ether, tetrahydrofuran, dioxane and others; and acetic acid can be exemplified. As to the halogenating agent used in this halogenation reaction, halogen molecules such as bromine, chlorine and others; metal halides such as cupric bromide, cupric chloride, lithium chloride and others; thionyl chloride; N-halogenated succinimides such as N-chlorosuccinimide, N-bromosuccinimide and others can be exemplified.

The halogenating agent may generally be used in a large excess amount. The halogenation is carried out generally at 0° to 150° C., preferably at 0° to 120° C., and is completed in 1 to 24 hours.

The reaction of a compound (29) with a compound (30) can be carried out in a suitable solvent, in the presence of a basic compound. As to the solvent used in this reaction, ethers such as diethyl ether, dioxane, tetrahydrofuran, ethylene glycol dimethyl ether, diethylene glycol dimethyl ether and others; aromatic hydrocarbons such as benzene, toluene, xylene and others; aliphatic hydrocarbons such as n-hexane, heptane, cyclohexane and others; aprotic polar solvents such as N,N-dimethylformamide, dimethyl sulfoxide, hexamethylphosphoryl triamide and others can be exemplified. As to the basic compounds, inorganic basic compounds such as sodium hydroxide, potassium hydroxide, sodium carbonate, potassium carbonate, sodium hydrogen carbonate, potassium hydrogen carbonate, metallic sodium, metallic potassium, sodium amide, sodium hydride and others; alcoholates such as sodium methylate, sodium ethylate and otherss; organic basic compounds such as triethylamine, pyridine, N,N-dimethylaniline and others can be exemplified.

The reaction is generally carried out at a room temperature to 200° C., preferably at a room temperature to 150° C., and is completed in 1 to 24 hours. The ratio of the amount of the compound (30) to the amount of the compound (29) is generally at least an equimolar quantity, preferably an equimolar quantity to 2 times the molar quantity of the former is used to the latter.

Dihydropyridine derivatives represented by the general formula (1) can also be prepared by the methods as shown in the following reaction process formula-16 and -18.

Reaction process formula-16

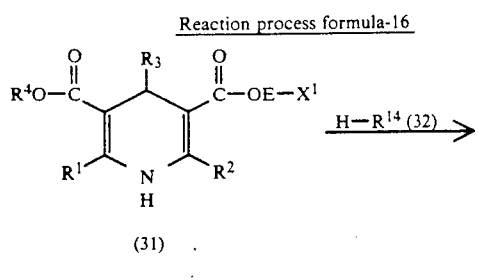

(31)

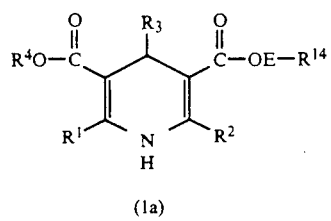

(1a)

[wherein $R^1$, $R^2$, $R^3$, $R^4$ and $X^1$ are the same as defined above; E is a lower alkylene group; $R^{14}$ is a 1,2,3,6-tetrahydropyridyl group which may have, as the substituent, a phenyl group which may have halogen atoms or lower alkyl groups as the substituents on the phenyl ring, group of the formula $R^6-(D')_o-Y-$ (wherein $R^6$, D', Y and o are the same as defined above)].

The reaction of a compound (31) with a compound (32) may be carried out in a suitable solvent, in the absence or presence of a basic compound. As to the solvent used in the reaction, halogenated hydrocarbons such as dichloromethane, dichloroethane, chloroform, carbon tetrachloride, and others; ethers such as diethyl ether, tetrahydrofuran, dioxane, ethylene glycol dimethyl ether and others; aliphatic hydrocarbons such as n-hexane, octane, cyclohexane and others; aromatic hydrocarbons such as benzene, toluene, xylene and others; aprotic polar solvents such as acetone, acetonitrile, N,N-dimethylformamide, dimethyl sulfoxide, hexamethylphosphoryl triamide and others can be exemplified. As to the basic compounds used in the reaction, inorganic basic compounds such as sodium hydroxide, potassium hydroxide, sodium carbonate, potassium carbonate, sodium hydrogen carbonate, sodium hydride and others; amines such as triethylamine, diisopropylethylamine, pyridine, quinoline and others can be exemplified. Further, the reaction can be carried out, if necessary, by adding an alkali metal iodied such as potassium iodied, sodium iodide or the like, or hexamethylphosphoryl triamide as the reaction accelarator. The reaction is carried out at a room temperature to 200° C., preferably at a room temperature to 120° C., and is completed in 1 to 24 hours.

The ratio of the amount of the compound (32) to the amount of the compound (31) is at least an equimolar quantity, preferably an equimolar quantity to 5 times the molar quantity of the former to the latter.

Among the compounds represented by the general formula (32), some of them are novel compounds and they can prepared by a method for example according to the following reaction process formula-17.

Reaction process formula-17

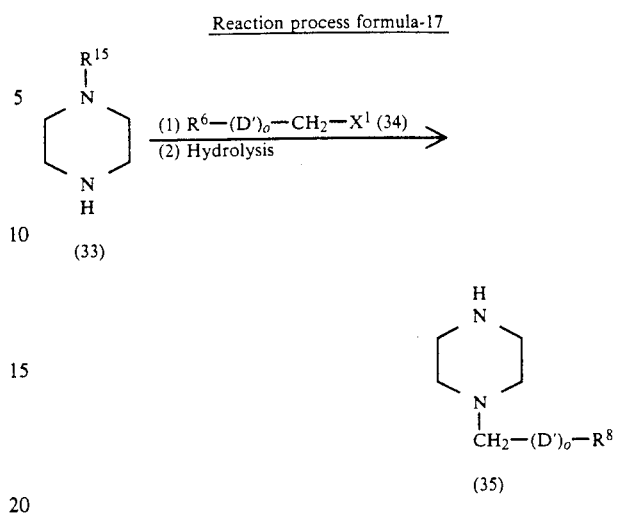

[wherein $R^8$, D', o and $X^1$ are the same as defined above; and $R^{15}$ is a lower alkanoyl group].

The reaction of a compound (33) with a compound (34) can be carried out under the same condition employed in the reaction of a compound (24) with a compound (25), and the hydrolysis followed by the reaction can be carried out under the same conditions employed in the hydrolysis of a compound (3g) in the above-mentioned reaction process formula-9.

Reaction process formula-18

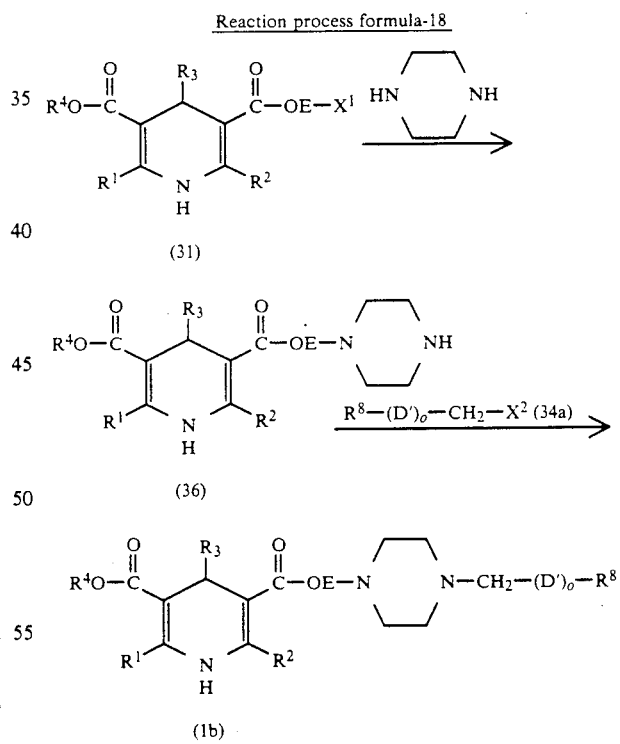

[wherein $R^1$, $R^2$, $R^3$, $R^4$, E, $X^1$, $R^8$, D' and o are the same as defined above; and $X^2$ is a halogen atom].

The reaction of a compound (31) with piperazine can be carried out under the same conditions employed in the reaction of a compound (31) with a compound (32). Further, the reaction of a compound (36) with a compound (34a) can be carried out under the same conditions employed in the reaction of a compound (24) with a compound (25).

Among the compounds represented by the general formula (1), those having basic groups can be converted into the corresponding salts by treating with pharmacologically acceptable acids. Examples of such acids including inorganic acids such as sulfuric acid, nitric acid, hydrochloric acid, hydrobromic acid and others; as well as organic acids such as oxalic acid, maleic acid, fumaric acid, malic acid, citric acid, benzoic acid and others.

Compound of the present invention thus prepared can easily be isolated and purified by a method usually employed in separation, such as precipitation, extraction, recrystallization, column chromatography, preparative thin layer chromatography and others.

Compound of the present invention represented by the general formula (1) contains inevitably its optical isomers, as well as those in different crystal forms.

Compound of the present invention represented by the general formula (1) can be administered, either singly or together with conventional pharmacologically acceptable carriers, to animals as well as to human beings. No particular restriction is made to the administration unit forms, thus compound of the present invention represented by the general formula (1) can be used in any desired administration unit form. Suitable administration unit forms including peroral administration unit forms such as tablets, granules and solutions; and parenteral administration unit forms such as injections.

Dosage of a compound represented by the general formula (1) as the active ingredient to be administered is not subjected to any particular restriction and can be selected from a wide range. For the purpose of attaining the desired pharmacological effects, it is recommended to select a dosage from the range of 0.06 to 10 mg/kg of the body weight/day. It is suggested also to contain 1 to 500 mg of the active ingredient in each of the desired administration unit form.

In the present invention, the desired peroral administration unit forms such as tablets, capsules and solutions can be prepared by conventional methods. For the purpose of shaping the administration unit form into the form of tablets, a compound of the present invention is mixed with pharmaceutically acceptable excipients such as gelatin, starch, lactose, magnesium stearate, talcum powder and gum arabic and others. Capsules can be prepared by mixing a compound of the present invention with an inert pharmaceutically acceptable fillers or diluents and filling the mixture obtained into rigid gelatin capsules or soft capsules. Sirups or elixiers may be prepared by mixing a compound of the present invention with a sweetening agent such as sucrose; anticeptice such as methyl- or propylparabens; colorants; seasoning agents and/or other suitable additives. Parenteral preparations can also be prepared by conventional methods, thus a compound of the present invention is dissolved in a sterilized liquid vehicle. As to the preferable vehicle, water or saline can be used. Liquid preparations having desired transparency, stability and parenteral use adaptability can be prepared by dissolving approximately 1 to 500 mg of the active ingredient in a solution of polyethylene glycol having the molecular weight of 200 to 5,000, which is soluble in both water and organic solvents. Desirably, such liquid preparations may contain a lubricant such as sodium carboxymethyl cellulose, methyl cellulose, polyvinyl pyrrolidone and polyvinyl alcohol. Said liquid preparations may also contain a bactericide and fungicide such as benzyl alcohol, phenol and thimerosal, and if necessary, an isotonic agent such as sucrose or sodium chloride, a local anesthetic, stabilizer and buffer solutions. Furthermore, additional ensurance of stability, the parenteral compositions may be freezed after filling and dehydrating steps by known lyophilization techniques. The lyophilized powder of the parenteral composition can be made again into a normal use from just before the use.

Preparation of Tablets 1,000 Tablets for peroral use, each containing 5 mg of methyl 3-(4-hydroxyphenyl)-2-propenyl 1,4-dihydro-2,6-dimethyl-4-(3-nitrophenyl)pyridine-3,5-dicarboxylate are prepared from the following formulation.

| Formulation | Amount (g) |
| --- | --- |
| Methyl 3-(4-hydroxyphenyl)-2-propenyl 1,4-dihydro-2,6-dimethyl-4-(3-nitrophenyl)pyridine-3,5-dicarboxylate | 5 |
| Lactose (Japanese Pharmacopoeia official drug grade) | 50 |
| Corn starch (Japanese Pharmacopoeia official drug grade) | 25 |
| Crystalline cellulose (Japanese Pharmacopoeia official drug grade) | 25 |
| Methyl cellulose (Japanese Pharmacopoeia official drug grade) | 1.5 |
| Magnesium stearate (Japanese Pharmacopoeia official drug grade) | 1 |

Methyl 3-(4-hydroxyphenyl)-2-propenyl 1,4-dihydro-2,6-dimethyl-4-(3-nitrophenyl)pyridine-3,5-dicarboxylate, lactose, corn starch and crystalline cellulose are mixed well, and the mixture is granulated with 5%-methyl cellulose aqueous solution, then the granules are passed through a 200 mesh sieve and then dried carefully. The dried granules are passed through a 200 mesh sieve and mixed with magnesium stearate, then pressed into the form of tablets.

Preparation of capsules 1,000 Capsules of two-piece rigid gelatin capsules for peroral use, each containing 10 mg of methyl 3-(4-hydroxyphenyl)-2-propynyl 1,4-dihydro-2,6-dimethyl-4-(3-nitrophenyl)pyridine-3,5-dicarboxylate are prepared by using the following formulation.

| Formulation | Amount (g) |
| --- | --- |
| Methyl 3-(4-hydroxyphenyl)-2-propynyl 1,4-dihydro-2,6-dimethyl-4-(3-nitrophenyl)pyridine-3,5-dicarboxylate | 10 |
| Lactose (Japanese Pharmacopoeia official drug grade) | 80 |
| Starch (Japanese Pharmacopoeia official drug grade) | 30 |
| Talcum powder (Japanese Pharmacopoeia official drug grade) | 5 |
| Magnesium stearate (Japanese Pharmacopoeia official drug grade) | 1 |

The above-mentioned ingredients are finely ground, then mixed sufficiently to a uniform mixture and filled into gelatin capsules of a size having desired size for peroral administration.

Preparation of injection solution

A sterile aqueous solution suitable for parenteral use is prepared from the following formulation.

| Formulation | Amount (g) |
| --- | --- |
| Methyl 3-(4-hydroxyphenyl)-2-propenyl 1,4-dihydro-2,6-dimethyl-4-(3-nitrophenyl)pyridine-3,5-dicarboxylate | 1 |
| Polyethylene glycol (M. W. = 4,000) (Japanese Pharmacopoeia official drug grade) | 0.9 |
| Sodium chloride (Japanese Pharmacopoeia official drug grade) | 0.9 |
| Polyoxyethylene sorbitan monooleate (Japanese Pharmacopoeia official drug grade) | 0.4 |
| Sodium metabisulfite | 0.1 |
| Methyl p-hydroxybenzoate (Japanese Pharmacopoeia official drug grade) | 0.18 |
| Propyl p-hydroxybenzoate (Japanese Pharmacopoeia official drug grade) | 0.02 |
| Distilled water for injection | 100 (ml) |

The above-mentioned methyl p-hydroxybenzoate, propyl p-hydroxybenzoate, sodium metabisulfite and sodium chloride are dissolved in about a half volume of distilled water at 80° C. under stirring condition. The solution obtained is cooled to 40° C., then methyl 3-(4-hydroxyphenyl)-2-propenyl 1,4-dihydro-2,6-dimethyl-4-(3-nitrophenyl)pyridine-3,5-dicarboxylate, polyethylene glycol and polyoxyethylene sorbitan monooleate are dissolved in the solution. Thus obtained solution is further mixed with the distilled water for injection so as to make it into the final volume, then sterilized by sterile filtration with a suitable filter paper.

The present invention will be illustrated more specifically by way of the following examples, in which the preparations of the compounds to be used for the starting materials will be shown in Reference Examples and the preparations of the objective compounds will be shown in Examples. The present invention, however will not restricted to these examples.

REFERENCE EXAMPLE 1

To 20 g of p-hydroxybenzaldehyde and 32.5 g of monoethyl malonate were added 6 ml of pyridine and 0.2 ml of piperidine, then the mixture thus obtained was heated at 100 to 110° C. for 10 hours under stirring. The reaction mixture was then cooled, extracted with chloroform, and the chloroform layer was washed with a saturated aqueous solution of potassium hydrogen sulfite and water in this order, the chloroform extract was dried with magnesium sulfate. The solvent was removed by evaporation and the residue thus obtained was crystallized from isopropyl ether-n-hexane to yield 25.2 g of ethyl 4-hydroxycinnamate. Light yellow indefinite form crystals. Melting point: 70°-71° C.

REFERENCE EXAMPLE 2

By using 20 g of 3-hydroxybenzaldehyde and 32.5 g of monoethyl malonate as the starting materials, and by a method similar to that described in Reference Example 1, under reaction conditions similar thereto, there was prepared 25.5 g of ethyl 3-hydroxycinnamate. Melting point: 65°-68° C. (from isopropyl ether)

REFERENCE EXAMPLE 3

By using 25.8 g of 4-hydroxy-3-chlorobenzaldehyde and 32.5 g of monoethyl malonate as the starting materials, and by a method similar to that described in Reference Example 1, under reaction conditions similar thereto, there was prepared 46 g of ethyl 4-hydroxy-3-chlorocinnamate. Colorless prism-like crystals (from methylene chloride). Melting point: 118°-119° C.

REFERENCE EXAMPLE 4

To 30 ml of anhydrous ether solution containing 5 g of ethyl 4-hydroxycinnamate was added 7.1 ml of dihydropyran and 50 mg of p-toluenesulfonic acid were added, the mixture was stirred at a room temperature for 2 hours, the reaction mixture was neutralized with 1%-sodium hydroxide solution, washed with water, and dried with anhydrous sodium sulfate. The solvent was removed by evaporation to yield 6.8 g of ethyl 4-(2-tetrahydropyranyloxy)cinnamate. Colorless indefinite form crystals. Melting point: 52°-53° C.

REFERENCE EXAMPLE 5

50 Milliliters of anhydrous ether solution containing 6.8 g of ethyl 4-(2-tetrahydropyranyloxy)cinnamate was added dropwise to an anhydrous ether solution containing 0.47 g of lithium aluminium hydride being cooled at −30° C. After the addition was finished, the reaction mixture was stirred for 1 hour at the same temperature, then the temperature of the reaction mixture was gradually elevated up to −10° C., then a saturated aqueous solution of sodium sulfate was gradually added to the reaction mixture, and the precipitates formed were removed by filtration. The filtrate was dried with anhydrous sodium sulfate, then concentrated to dryness, the residue thus obtained was treated by means of silica gel column chromatography (eluent: chloroform) to yield 3.2 g of 4-(2-tetrahydropyranyloxy)cinnamyl alcohol in the form of colorless oily substance. Refractive index: $n_D^{22}$ 1.5520.

REFERENCE EXAMPLE 6

15 Grams of 4-(2-tetrahydropyranyloxy)cinnamyl alcohol and 5.2 g of sodium acetate were suspended in anhydrous methylene chloride, then to this suspension was added in one time 18 g of pyridium chlorochromate under ice-cooled condition. The reaction mixture was stirred for 1 hour at the same temperature, then the temperature was elevated to a room temperature, and the reaction mixture wa stirred for additional 1 hour. 100 Milliliters of ether was added to the reaction mixture, the whole mixture was filtered with Celite (a trademark for diatomaceous product manufactured by and sold from Johns-Manville Products Corp., Celite Division, New York, N.Y., U.S.A.), the filtrate was concentrated and the residue thus obtained was treated by silica gel column chromatography. Recrystallization from ether to yield 3.5 g of 4-(2-tetrahydropyranyloxy)-cinnamyl aldehyde in the form of colorless needle-like crystals. Melting point: 65°-67° C.

REFERENCE EXAMPLE 7

5.6 Grams of triethyl phosphonoacetate was added dropwise under stirring condition at a room temperature to a tetrahydrofuran solution containing 1.06 g of 60%-sodium hydride, then the reaction mixture was further stirred at 40° C. for 1 hour. The reaction mixture was cooled to a room temperature, then a tetrahydrofuran solution containing 5.6 g of 4-(2-tetrahydropyranyloxy)cinnamyl aldehyde was added thereto, and stirred at a room temperature for 2 hours, then the reaction mixture was poured into 100 ml of water. The whole mixture was extracted with ether, and the ether layer was washed with water, and a saturated aqueous solution of sodium chloride in this order, then dried with anhydrous sodium sulfate. Recrystallization from isopropyl ether to yield 3.8 g of ethyl 5-[4-(2-tetrahydropyranyloxy)phenyl]-2(E),4(E)-pentadienoate in the form of colorless needle-like crystals. Melting point: 66°-67.5°.

REFERENCE EXAMPLE 8

To 30 ml of anhydrous benzene solution containing 3.6 g of ethyl 5-[4-(2-tetrahydropyranyloxy)phenyl]-2(E),4(E)-pentadienoate was added dropwise 15 ml of diisobutyl aluminium hydride (25% by weight/by volume) under water-cooled condition and the reaction mixture was stirred at a room temperature for 2 hours. The reaction mixture was then poured into a saturated aqueous solution of ammonium chloride and stirred at a room temperature for 2 hours. The insoluble matters were treated with Celite, and the insoluble matters were washed with ether. The organic layer was washed with water and dried with anhydrous sodium sulfate, then concentrated to obtain the residue. The residue was recrystallized from chloroform-n-hexane to yield 2.8 g of 5 [4-(2-tetrahydropyranyloxy)phenyl]-2(E),4(E)-pentadienol in the form of colorless needle-like crystals. Melting point: 54°-58° C.

REFERENCE EXAMPLE 9

25 Grams of p-hydroxyacetophenone, 50 ml of dihydropyrane and 0.25 g of p-toluenesulfonic acid were stirred at a room temperature for 2 hours in anhydrous ether. Then the reaction mixture was neutralized with 1N-sodium hydroxide and washed with water and a saturated sodium chloride aqueous solution in this order, then dried with anhydrous sodium sulfate. The product was concentrated to yield 34 g of 4-(2-tetrahydropyranyloxy)-acetophenone. Colorless prism-like crystals. Melting point: 79°-83° C.

REFERENCE EXAMPLE 10

45.8 Grams of triethyl phosphonoacetate and an anhydrous tetrahydrofuran solution containing 8.7 g of 60%-sodium hydride were stirred at 40° C. for 1 hour, the reaction mixture was cooled and 30 g of 4-(2-tetrahydropyranyloxy)acetophenone was added to the reaction mixture. The whole reaction mixture was refluxed for 4 hours by heating, then the solvent was removed by evaporation, the residue thus obtained was extracted with ether and washed with water, than dried. The extract was concentrated and the residue thus obtained was treated by means of silica gel column chromatography to yield 27.5 g of ethyl 3-methyl-p-(2-tetrahydropyranyloxy)cinnamate in the form of light yellow oily substance.

$^1$H-NMR (90 MHz, CDCl$_3$) δ: 1.29 (3H, t, J=6 Hz), 1.4-2.1 (6H, m), 2.49 (3H, d, J=1 Hz), 3.3-3.9 (2H, m), 4.10 (2H, q, J=6 Hz), 5.3-5.45 (1H, m), 6.03 (1H, d, J=1 Hz), 6.9-7.4 (4H, m)

REFERENCE EXAMPLE 11

To a tetrahydrohydrofuran solution containing 27.5 g of ethyl 3-methyl-p-(2-tetrahydropyranyloxy)-cinnamate was added dropwise 118 ml of diisobutyl aluminium hydride (25% by weight/volume) at a room temperature. After 2 hours, the reaction mixture was poured into an ice-cooled ammonium chloride aqueous solution, and the insoluble matters were removed by filtration. The filtrate was washed with water then dried with anhydrous sodium sulfate and concentrated. The residue thus obtained was purified by means of silica gel column chromatography to yield 12.7 g of 3-methyl-p-(2-tetrahydropyranyloxy)cinnamyl alcohol in the form of colorless oily substance.

$^1$H-NMR (90 MHz, CDCl$_3$) δ: 1.5-2.0 (6H, m), 2.0 (3H, s), 3.3-4.0 (2H, m), 4.1-4.3 (3H, m), 5.26-5.4 (1H, m), 5.81 (1H, t, J=6 Hz), 6.8-7.5 (4H, m).

REFERENCE EXAMPLE 12

To a carbon disulfide solution containing 53 g of aluminium chloride and 26.2 g of thioanisol was added dropwise under an ice-cooled condition 24.0 ml of γ-chlorobutyryl chloride. After 1 hour and 30 minutes, the reaction mixture was poured into ice-water and the insoluble matters were collected by filtration, dissolved in chloroform. The chloroform solution was washed with water and dried with anhydrous sodium sulfate, and concentrated to dryness. Recrystallization from methanol to yield 36.2 g of γ-chloro-4-methylthiobutyro-phenone in the form of light yellow prism-like crystals. Melting point: 75°-76° C.

REFERENCE EXAMPLE 13

35 Grams of γ-chloro-4-methylthiobutyrophenone, 34 ml of 1,8-diazabicyclo[5,4,0]undecene-7 (DBU) and 150 ml of acetonitrile were refluxed for 4 hours, then 500 ml of water was added to the reaction mixture, and the whole mixture was extracted with ether. The ether extract was washed with water, dried and the solvent was removed by evapolation. The residue thus obtained was recrystallized from methanol to yield 24.6 g of cyclopropyl (4-methylthiophenyl)ketone as in the form of light yellow prism-like crystals. Melting point: 76°-76.5° C.

REFERENCE EXAMPLE 14

To 200 ml of methanol solution containing 24 g of cyclopropyl (4-methylthiophenyl)ketone was added slowly 9.4 g of sodium borohydride under an ice-cooled condition, the reaction mixture was stirred for 2 hours. Then an adequate amount of acetone was added to the reaction mixture and concentrated under a reduced pressure. To the residue thus obtained was added chloroform, and the chloroform solution was washed with water, dried with anhydrous sodium sulfate, and the solvent was removed by evaporation to yield 18 g of 1-(cyclopropyl, hydroxylmethyl)-4-methylthiobenzene as in the form of colorless oily substance.

NMR (90 MHz, CDCl$_3$) δ: 0.2-0.7 (4H, m), 0.9-1.4 (1H, m), 1.4-2.0 (6H, m), 3.2-3.7 (2H, m), 5.17-5.3 (1H, m), 6.8-7.3 (8H, m).

REFERENCE EXAMPLE 15

To 10 ml of dioxane solution containing 5 g of 1-(cyclopropyl, hydroxymethyl)-4-methylthiobenzene was added dropwise 6 ml of 47% of hydrobromic acid under an ice-cooled condition, then the mixture was stirred for 30 minutes, and the reaction mixture was concentrated under a reduced pressure. To the residue thus obtained was added water, then extracted with ether, the extract was washed with water and dried with anhydrous sodium sulfate, and concentrated to dryness. The residue was recrystallized from methanol to yield 2.2 g of 4-(4'-methylthiophenyl)-3(E)-butenylbromide in the form of colorless flake-like crystals. Melting point: 54°-56° C.

REFERENCE EXAMPLE 16

10 Grams of p-iodophenol, 8 ml of dihydropyrane and a catalytic amount of p-toluenesulfonic acid was dissolved in 30 ml of anhydrous ether, all of these were mixed together and stirred at a room temperature for 2 hours. The reaction mixture was washed with water, dried then the solvent was removed by evaporation to yield 12.4 g of 4-(2-tetrahydropyranyloxy)-1-iodobenzene in the form of yellow oily substance. Boiling point: 84°–87° C. (at 25 mm Hg).

REFERENCE EXAMPLE 17

6.25 Grams of triethyl phosphonocrotonate was added dropwise to a tetrahydrofuran solution containing 1.06 g of 60%-sodium hydride at a room temperature, the reaction mixture was stirred for 1 hour at 40° C. The temperature of the reaction mixture was cooled to a room temperature, then a tetrahydrofuran solution containing 5.0 g of p-(2-tetrahydropyranyloxy)benzaldehyde was added to the reaction mixture, and stirred at a room temperature for 2 hours, then poured into 100 ml of water. The whole mixture was extracted with ether, the ether extract was washed with water and a saturated sodium chloride aqueous solution in this order, then dried with anhydrous sodium sulfate. The solvent was removed by evaporation, the residue thus obtained was purified by means of silica gel column chromatography (eluent: hexane-chloroform), next recrystallized from isopropyl ether to yield 4.01 g of ethyl 5-[4-(2-tetrahydropyranyloxyphenyl)]-2(E),4(E)-pentadienoate. Colorless needle-like crystals. Melting point: 66°–67.5° C.

REFERENCE EXAMPLE 18

20 Grams of p-tetrahydropyranyloxyiodobenzene and 70 ml of anhydrous pyridine containing 11.3 g of copper (I) 3-acetyloxy-1-propyn-1-ide were refluxed for 6 hours under an atmosphere of argon gas. After the reaction was finished the reaction mixture was poured into water and the whole mixture was extracted with chloroform. The chloroform layer was washed with water, dried and the solvent was removed by evaporation. The residue thus obtained was purified by means of a silica gel column chromatography (eluent: chloroform: n-hexane=1:1) to yield 8 g of 4-[4-(2-tetrahydropyranyloxy)phenyl]-3-butynyl acetate in the form of colorless oily substance.

$^1$H-NMR (60 MHz, CDCl$_3$) δ: 6.98 (2H, d, J=8 Hz), 6.63 (2H, d, J=8 Hz), 6.15 (1H, m), 4.05 (2H, t, J=6 Hz), 3.3–3.7 (2H, m), 2.58 (2H, t, J=6 Hz), 1.97 (3H, s), 1.5–1.9 (6H, m).

REFERENCE EXAMPLE 19

To an anhydrous tetrahydrofuran solution containing 2.4 g of 4-[4-(2-tetrahydropyranyloxy)phenyl]-3-butynylacetate was added 1 g of lithium aluminium hydride and the mixture was refluxed for 12 hours. After the reaction was finished, a saturated sodium sulfate aqueous solution was slowly added to the reaction mixture, and the precipitates formed were removed by filtration, then the filtrate was dried with anhydrous sodium sulfate, and concentrated to dryness. The residue thus obtained was purified by means of a silica gel column chromatography to yield 2 g of 4-[(2-tetrahydropyranyloxy)phenyl]-3(E)-butenylalcohol as in the form of colorless oily substance.

$^1$H-NMR (90 MHz, CDCl$_3$) δ: 1.5–2.1 (6H, m), 2.43 (2H, q, J=6 Hz), 3.4–4.0 (5H, m), 5.37 (1H, m), 6.03 (1H, d, t, J=16 Hz, 6 Hz), 6.40 (1H, d, J=16 Hz), 6.97 (2H, d, J=9 Hz), 7.25 (2H, d, J=9 Hz).

REFERENCE EXAMPLE 20

15 Grams of 1-iodo-4-(1-ethoxyethoxy)benzene, 6 g of propargyl acetate, 0.26 g of triphenylphosphine, 0.09 g of palladium chloride and 20 ml of diethylamine solution of cuprous iodide were stirred at 40°–50° C. for 1 hour. After the reaction was finished, the reaction mixture was poured into water, and extracted with diethyl ether. The ether extract was washed with water, dried and the solvent was removed by evaporation, then the residue thus obtained was purified by means of a silica gel column chromatography (eluent: dichloromethane: n-hexane=1:1 and dichloromethane) to yield 10.1 g of 3-[4-(1-ethoxyethoxy)phenyl]propargyl acetate.

N. M. R. (CDCl$_3$) δ: 1.17 (3H, t, J=7 Hz), 1.47 (3H, d, J=5 Hz), 2.09 (3H, s), 3.3–3.9 (2H, m), 4.87 (2H, s), 5.37 (1H, q, J=5 Hz), 6.92 [2H, d, J=9 Hz), 7.37 (2H, q, J=9 Hz).

REFERENCE EXAMPLE 21

To 50 ml of methanol solution containing 10 g of 3-[4-(1-ethoxyethoxy)phenyl]propargyl acetate, were added 1.5 g of 5%-Pd-BaSO$_4$ and 10 drops of quinoline, and the mixture was catalytically reduced. After the reaction was finished, the reaction mixture was filtered, and the filtrate was allowed to evaporation, the residue thus obtained was purified by means of a silica gel column chromatography (eluent: dichloromethane and dichloromethane:methanol=100:1) to obtain 3 g of 4(Z)-(1-ethoxyethoxy)cinnamyl acetate and 4 g of 4(Z)-hydroxycinnamyl acetate. Thus obtained 4 g of 4(Z)-hydroxycinnamyl acetate was dissolved in 20 ml of anhydrous ether, to this solution was added 50 mg of p-toluenesulfonic acid and 10 ml of ethyl vinyl ether, and the whole mixture was refluxed for 3 hours. The reaction mixture was then washed with 5%-sodium hydroxide aqueous solution and water in this order, and dried. The solvent was removed by evaporation to yield 4.8 g of 4(Z)-(1-ethoxyethoxy)cinnamyl acetate.

N. M. R. (CDCl$_3$) δ: 1.21 (3H, t, J=7 Hz), 1.50 (3H, d, J=5 Hz), 2.09 (3H, s), 3.24–3.64 (1H, m), 3.70–3.90 (1H, m), 4.84 (2H, dd, J=6.5 Hz, 1.5 Hz), 5.40 (1H, q, J=5 Hz), 5.73 (1H, dt, J=11.5 Hz, 6.5 Hz), 6.60 (1H, dm, J=11.5 Hz), 6.98 (2H, d, J=9 Hz), 7.15 (2H, d, J=9 Hz).

REFERENCE EXAMPLE 22

7.8 Grams of 4[Z)-(1-ethoxyethoxy)cinnamyl acetate and 50 ml of methanol solution containing 5 g of potassium carbonate were stirred at a room temperature for 2 hours. The solvent was removed by evaporation, and to the residue thus obtained was added water and extracted with ether. The ether extract was washed with water, dried and the solvent remove by evaporation to yield 4(Z)-(1-ethoxyethoxy)cinnamyl alcohol.

N. M. R. (90 MHz, CDCl$_3$) δ: 1.19 (3H, t, J=7 Hz), 1.48 (3H, d, J=5 Hz), 3.4–3.9 (2H, m), 4.39 (2H, dd, J=6 Hz, J=2 Hz), 5.36 (1H, q, J=5 Hz), 5.75 (1H, dt, J=11 Hz, J=6 Hz), 6.45 (1H, dm, J=11 Hz), 6.95, 7.10 (4H, AB-q, J=9 Hz).

REFERENCE EXAMPLE 23

8 Milliliters of 85% sodium hydroxide aqueous solution mixed with 46 g of ethylene glycol was heated at 40°–50° C., and 15 g of cinnamyl bromide was added dropwise thereto. After the addition was finished, the reaction mixture was heated at 100°–110° C. for 2 hours. The reaction mixture was allowed to cool, and poured into 50 ml of water, then extracted with ether. The ether extract was washed with water and a saturated aqueous solution of sodium chloride in this order, and dried with anhydrous sodium sulfate. The solvent was removed by evaporation, the residue thus obtained was purified by means of a silica gel column chromatography (eluent: chloroform) to yield 5.5 g of 2-[3-phenyl-2(E)-propenyloxy]ethanol.

N. M. R. CDCl$_3$ (90 MHz) δ: 2.20 (1H, t, J=6 Hz), 3.50-3.85 (4H, m), 4.18 (2H, d, J=6 Hz), 6.23 (1H, dt, J=6 Hz, J=16 Hz), 6.57 (1H, d, J=16 Hz), 7.20-7.50 (5H, m).

REFERENCE EXAMPLE 24

5.33 Grams of 60% sodium hydride was suspended in 25 ml of dimethylformamide, and 9.3 ml of ethylene glycol was added dropwise thereto. After the addition was finished the reaction mixture was stirred at 45° C. for 2 hours. The reaction mixture was ice-cooled, then 6.5 g of 3-phenylpropargyl bromide was added dropwise to the reaction mixture and stirred at the same temperature for 1 hour. After the reaction was finished, the reaction mixture was poured into 200 ml of water, and the whole mixture was extracted with ether. The ether extract was washed with water and dried with anhydrous magnesium sulfate, and the solvent was removed by evaporation. The residue thus obtained was purified by means of a silica gel column chromatography (eluent: chloroform:n-hexane=3:1) to yield 2.4 g of 2-(3-phenyl-2-propionyloxy)ethanol. Refractive index: n$_D^{24}$ 1.5590.

REFERENCE EXAMPLE 25

6.5 Grams of propargyl bromide, 0.32 g of tetrabutylammonium bromide and 2.7 g of sodium hydroxide were dissolved in 20 ml of methylene chloride and 8 ml of water, and this solution was refluxed for 2 hours. After the reaction mixture was cooled, the organic layer was collected by separation, washed with water, dried with anhydrous magnesium sulfate. The solvent was removed by evaporation, the residue thus obtained was purified by means of a silica gel column chromatography (eluent: chloroform:n-hexane=2:1) to yield 4.0 g of 2-(3-phenyl-2-propionylthio)ethanol. Refractive index: n$_D^{22}$ 1.6078.

REFERENCE EXAMPLE 26

4.3 Grams of 2-mercaptoethanol, 10 ml of 40% sodium hydroxide aqueous solution, 0.2 g of tetrabutylammonium bromide and 40 ml of methylene chloride were heated at 40°-45° C., then 20 ml of methylene chloride solution containing 10 g of cinnamyl bromide was added dropwise thereto. The reaction mixture was stirred vigorously at the same temperature for 4-5 hours. The organic layer was collected by separation and washed with water, dried with anhydrous sodium sulfate. The solvent was removed by evaporation, the residue thus obtained was distilled under a reduced pressure to yield 8.6 g of 2-(3-phenyl-2(E)-propionylthio)ethanol. Boiling point: 150°-153° C. (1 mm Hg).

N. M. R. CDCl$_3$ (90 MHz) δ: 2.16 (1H, t, J=6 Hz), 2.70 (2H, t, J=6 Hz), 3.30 (2H, d, J=6 Hz), 3.70 (2H, q, J=6 Hz), 6.14 (1H, dt, J=6 Hz, J=16 Hz), 6.40 (1H, d, J=16 Hz), 7.20-7.60 (5H, m).

REFERENCE EXAMPLE 27

12.5 Grams of cinnamyl chloride and 21 g of 2-methylaminoethanol were dissolved in 100 ml of ethanol, and the solution was refluxed for 5 hours. The solvent was removed by evaporation, to the residue thus obtained was added water and washed with n-hexane. To the water layer was added 3N-sodium hydroxide aqueous solution to adjust its pH to 10-11, and extracted with ether. The ether extract was washed with water and dried with anhydrous sodium sulfate, and the solvent was removed by evaporation. The residue was purified by means of a silica gel column chromatography (eluent: chloroform:methanol=25:1) to yield 15 g of 2-[N-methyl-N-(3-phenyl-2(E)-propenyl)amino]ethanol.

N. M. R. CDCl$_3$ (90 MHz) δ: 2.30 (3H, s), 2.55 (2H, t, J=7 Hz), 2.90 (1H, s), 3.20 (2H, d, J=7 Hz), 3.60 (2H, t, J=7 Hz), 6.20 (1H, dt, J=7 Hz, J=16 Hz), 6.48 (1H, d, J=16 Hz), 7.25-7.50 (5H, m).

REFERENCE EXAMPLE 28

By a method similar to that described in Reference Example 27, by using a suitable starting material, the following compound was prepared.

2-[N-Methyl-N-(3-phenyl-2-propynyl)amino]ethanol Boiling point: 124°-126° C. (1 m 2 mm Hg) Refractive index: n$_D^{24}$ 1.5589

REFERENCE EXAMPLE 29

5 Grams of cinnamyl bromide, 5 g of anhydrous piperazine and 50 ml of acetone solution containing 8.4 g of anhydrous potassium carbonate were refluxed for 6 hours. To the reaction mixture was added water and the whole mixture was extracted with chloroform. The chloroform layer was washed with water, dried and the solvent was removed by evaporation. 2.2 Grams of 1-acetyl-4-cinnamylpiperazine thus obtained was dissolved in 80% of methanol, and 2 g of potassium hydroxide was added thereto, then the mixture was refluxed for 8 hours. To the reaction mixture was added water, and the whole mixture was extracted with chloroform, washed with water, dried, and chloroform was removed by evaporation. The residue thus obtained was purified by means of a silica gel column chromatography (eluent: chloroform and chloroform:methanol=30:1) to yield 1.2 g of N-cinnamylpiperazine.

N. M. R. CDCl$_3$ δ: 2.34 (1H, s), 2.46 (4H, m, J=5 Hz), 2.92 (4H, m, J=5 Hz), 3.13 (2H, d, J=6 Hz), 6.23 (1H, dt, J=15 Hz, 6 Hz), 6.82 (1H, d, J=15 Hz), 7.2-7.5 (5H, m).

REFERENCE EXAMPLE 30

To 150 ml of anhydrous carbon tetrachloride solution containing 116 g of methyl acetoacetate was added dropwise 51 ml of bromine at below 5° C. After the addition was finished the reaction mixture was stirred overnight, then the reaction mixture was poured into ice-water, washed with a diluted sodium carbonate aqueous solution five times, then with a saturated sodium chloride aqueous solution, and dried with anhydrous calcium chloride. The solvent was removed by evaporation to yield 170 g of methyl 4-bromoacetoacetate.

REFERENCE EXAMPLE 31

1.6 Grams of 60% sodium hydride was suspended in 80 ml of anhydrous dimethoxyethane, then 40 ml of dimethoxyethane solution containing 8 g of methyl 4bromoacetoacetate was added dropwise thereto at −40° to −50° C. At the same temperature, lithium N-methylcinnamylamide prepared from 20 ml of dimethoxyethane solution containing 5.9 g of N-methylcinnamylamine and 40 ml of 1N-n-butyl lithium was added dropwise. After the addition was finished, the reaction mixture was stirred at 65°-70° C. for 15 hours. The reaction mixture was poured into an ice-water and the whole mixture was extracted with diethyl ether. The extract was washed with water, dried and the solvent was removed by evaporation, the residue thus obtained was purified by means a silica gel column chromatography (eluent: dichloromethane and dichloromethane:methanol= 50:1) to yield 1.8 g of 4-(N-methyl-E-cinnamylamino)acetoacetate.

N. M. R. CDCl$_3$ δ: 2.32 (3H, s), 3.22 (2H, d, J=6 Hz), 3.31 (2H, s), 3.51 (2H, 2), 3.68 (3H, s), 6.18 (1H, dt, J=16 Hz, 6 Hz), 6.50 (1H, d, J=16 Hz), 7.0–7.5 (5H, m).

REFERENCE EXAMPLE 32

4 Grams of 60% sodium hydride was suspended in 150 ml of anhydrous dimethoxyethane and the suspension was cooled to −30° C. Then, 19.4 g of methyl 4-bromoacetoacetate was added dropwise to the suspension and stirred for 1 hour. Further, at the same temperature, an anhydrous dimethoxyethane solution of sodium cinnamyl alcoholate prepared from 13.4 g of cinnamyl alcohol, 4 g of 60% of sodium hydride and 75 ml of dimethoxyethane was added dropwise thereto, and the reaction mixture was refluxed for 15 hours. After the reaction mixture was cooled to a room temperature, the reaction mixture was poured into 1N-hydrochloric acid being ice-cooled, and the whole mixture was extracted with ether. The ether extract was washed with water and dried with anhydrous sodium sulfate, and the solvent was removed by evaporation. The residue was purified by means of a silica gel column chromatography (eluent: methanol:dichloromethane=1:20) to yield 6 g of methyl 4(E)-cinnamyloxyacetoacetate Refractive index: n$_D^{20}$ 1.5402

REFERENCE EXAMPLE 33

By a method similar to that described in Example 32, by using a suitable starting material, there was prepared the following compounds.

Methyl 4-[4(E)-(1-ethoxyethoxy)cinnamyloxy]acetoacetate
Refractive index: n$_D^{20}$=1.5232

REFERENCE EXAMPLE 34

A mixture of 9 g of 4(E)-(1-ethoxyethoxy)-cinnamyl alcohol and 0.5 ml of triethylamine was heated at 70°-80° C., and 6 g of diketene was slowly added dropwise thereto. After the addition was finished, the reaction mixture was heated at 110°-120° C. for 30 minutes. After the reaction was completed, the solvent was removed by evaporation under a reduced pressure, and the residue thus obtained was purified by means of a silica gel column chromatography (eluent: diethyl ether: n-hexane=1:3) to yield 8.8 g of 4(E)-(1-ethoxyethoxy)cinnamyl acetoacetate. Refractive index: $D_{24}$ 1.5305

N. M. R. CDCl$_3$ (90 MHz) δ: 1.17 (3H, t, J=7 Hz), 1.48 (3H, d, J=6 Hz), 2.25 (3H, s), 3.48 (2H, s), 3.40-3.85 (2H, m), 4.75 (2H, d, J=6 Hz), 5.36 (1H, q, J=6 Hz), 6.18 (1H, dt, J=6 Hz, J=16 Hz), 6.94 (2H, d, J=9 Hz), 7.28 (2H, d, J=9 Hz).

REFERENCE EXAMPLE 35

To 400 ml of acetonitrile solution containing 30 g of 2-iodoethyl methyl 2,6-dimethyl-4-(3-nitrophenyl)-1,4-dihydropyridine-3,5-dicarboxylate was added 26.6 g of piperazine, and the mixture was stirred at a room temperature overnight. After the reaction was finished, the insoluble matters were removed by filtration, then chloroform was added to the filtrate, the chloroform layer was washed with a saturated sodium hydrogen carbonate aqueous solution and water in this order, and dried with anhydrous sodium sulfate. The reaction mixture was concentrated by evaporating the solvent, and the residue thus obtained was purified by means of a silica gel column chromatography (eluent: dichloromethane:methanol:triethylamine=100:10:1) to yield 21 g of methyl 5-[2-(1-piperazinyl)ethyl]2,6-dimethyl-4-(3-nitrophenyl)-1,4-dihydropyridine-3,5-dicarboxylate as in the form of light yellow indefinite form crystals.

N. M. R. CDCl$_3$ (200 MHz) δ: 1.892 (1H, bs), 2.366 (3H, s), 2.379 (3H, s), 2.40-2.50 (4H, m), 2.52-2.60 (2H, m), 2.80-2.90 (4H, m), 3.651 (3H, s), 4.08-4.28 (2H, m), 5.109 (1H, s), 5.947 (1H 7.3-8.2 (4H, m).

REFERENCE EXAMPLE 36

18.6 Grams of 5-acetyl-2,2-dimethyl-1,3-dioxane-4,6-dione and 50 ml tetrahydrofuran solution containing 22.2 g of 4-(1-ethoxyethoxy)cinnamyl alcohol were refluxed for 6 hours. After the reaction was completed, the solvent was removed by evaporation, and the residue thus obtained was purified by means of a silica gel column chromatography (eluent: ethyl acetate:n-hexane=1:4) to yield 5.8 g of 4-[(1-ethoxy)ethoxy]cinnamyl acetoacetate as in the form of an oily substance.

N. M. R. (CDCl$_3$) δ: 1.15 (3H, t, J=7 Hz), 1.44 (3H, d, J=5.4 Hz), 2.20 (3H, s), 3.31-3.95 (2H, m), 3.45 (2H, s), 4.71 (2H, d, J=6 Hz), 5.35 (1H, q, J=5.2 Hz), 6.10 (1H, dt, J=6.1 Hz, 15.3 Hz), 6.59 (1H, d, J=15.3 Hz), 6.91 (2H, d, J=9 Hz), 7.29 (2H, d, J=9 Hz).

IR (film): υ: 1650, 1730$^{-1}$.

EXAMPLE 1

5.4 Grams of 4-(2-tetrahydropyranyloxy)cinnamyl alcohol, 11.5 g of 1,4-dihydro-2,6-dimethyl-5-methoxycarbonyl-4-(3-nitrophenyl)pyridine-3-carboxylic acid and 7.1 g of DCC were dissolved in 30 ml of pyridine, and the reaction mixture was stirred at a room temperature overnight. 200 Milliliters of water was added to the reaction mixture and extracted with ethyl acetate. The extract was washed with water, a saturated potassium hydrogen sulfate aqueous solution, water and a saturated sodium chloride aqueous solution in this order, then dried and the solvent was removed by evaporation. The residue thus obtained was purified by means a silica gel column chromatography (eluent: chloroform) to yield 3.4 g of methyl 3-(4-tetrahydropyranyloxyphenyl)-2(E)-propenyl 1,4-dihydro-2,6-dimethyl-4-(3-nitrophenyl)-pyridine-3,5-dicarboxylate.

N. M. R. δ (CDCl$_3$): 1.4–2.0 (6H, m), 2.26 (6H, m), 3.53 (3H, s), 3.4–4.0 (2H, m), 4.58 (2H, d, J=6 Hz), 5.03 (1H, s), 5.30 (1H, t, J=3 Hz), 5.97 (1H, dt, Ja=6 Hz, Jb=16 Hz), 6.30 (1H, bs), 6.37 (1H, d, J=16 Hz), 6.88 (2H, d, J=9 Hz), 7.14 (2H, d, J=9 Hz), 7.20 (1H, t, J=6 Hz), 7.50 (1H, dt, Ja=2 Hz, Jb=6 Hz), 7.82 (1H, dt, Ja=2 Hz, Jb=tHz), 8.00 (1H, t, J=2 Hz).

EXAMPLE 2

3.4 Grams of methyl 3-(4-tetrahydropyranyloxyphenyl)2(E)-propenyl 1,4-dihydro-2,6-dimethyl-4-(3-nitrophenyl)pyridine-3,5-dicarboxylate was dissolved in 50 ml of methanol, then 0.2 g of p-toluenesulfonic acid was added to the solution and the whole mixture was stirred at a room temperature for 4 hours. The reaction mixture was neutralized by adding sodium hydrogen carbonate, and methanol was removed by evaporation. The residue thus obtained was purified by means of a silica gel column chromatography (eluent: chloroform), recrystallized from benzene-ether to yield 2 g of methyl 3-(4-hydroxyphenyl)-2(E)-propenyl 1,4-dihydro-2,6-dimethyl-4-(3-nitrophenyl)pyridine-3,5-dicarboxylate as in the form of light yellow powdery substance. Melting point: 137.5°–139° C.

EXAMPLE 3

To 20 ml of an anhydrous methylene chloride solution containing 1.6 g of tetramethylurea was added 1.9 g of oxalyl chloride at a room temperature and the mixture was refluxed for 2 hours, then 4.3 g of 1,4-dihydro-2,6-dimethyl-5-methoxycarbonyl-4-(3-nitrophenyl)-pyridine-3-carboxylic acid was added thereto, under an ice-cooled and stirred condition while the raction mixture was as in a suspended state, 1.7 g of 3-p-(2-tetrahydropyranyloxy)phenylpropargyl alcohol in 10 ml of anhydrous methylene chloride solution was added to the suspension and the whole mixture was stirred at a room temperature for 3 hours. Under an ice-cooled condition, the reaction mixture was poured in 1N-hydrochloric acid, and the organic layer was washed with water in three times and dried with anhydrous sodium sulfate, then solvent was removed by evaporation. The residue thus obtained was purified by means of a silica gel column chromatography (eluent: chloroform) to yield 2.8 g of methyl 3-[4-(2-tetrahydropyranyloxyphenyl))]-2-propynyl 1,4-dihydro-2,6-dimethyl-4-(3-nitrophenyl)pyridine-3,5-dicarboxylate in the form of light yellow indefinite form crystals.

EXAMPLE 4

2.7 Grams of methyl 3-[4-(2-tetrahydropyranyloxyphenyl)]-2-propynyl 1,4-dihydro-2,6-dimethyl-4-(3-nitrophenyl)pyridine-3,5-dicarboxylate was dissolved in 30 ml of methanol, then 10 mg of p-toluenesulfinic acid was added and the mixture was stirred for 1 hour. The reaction mixture was neutralized by adding a saturated sodium hydrogen carbonate aqueous solution, further 100 ml of water was added then the mixture was extracted with chloroform. The chloroform layer was washed with water in three times, then dried with anhydrous sodium sulfate, the solvent was removed by evaporation. The residue thus obtained was purified by means of a silica gel column chromatography (eluent: ethyl acetate:n-hexane=4:1), next recrystallized from tetrahydrofuran-n-hexane to yield 1.2 g of methyl 3-(4-hydroxyphenyl)-2-propynyl-1,4-dihydro-2,6-dimethyl-4-(3-nitrophenyl)pyridine-3,5-dicarboxylate in the form of yellow prism-like crystals.
Melting point: 173°–176° C.

EXAMPLE 5

To a mixture consisting of 1.9 of 1,4-dihydro-2,6-dimethyl-5-methoxycarbonyl-4-(3-nitrophenyl)pyridine-3-carboxylic acid, 0.78 ml of 30% sodium hydroxide aqueous solution and 15 ml of HMPA were added dropwise 1.5 g of 4-(4-methylthiophenyl)-3(E)-butenyl bromide. The mixture was stirred at a room temperature for 8 hours, then at 40°–45° C. for 5 hours, next the reaction mixture was poured into an ice-water and extracted with chloroform. The chloroform layer was washed with water, then dried with anhydrous sodium sulfate, and the solvent was removed by evaporation. The residue thus obtained was purified by means of a silica gel column chromatography (eluent: ethyl acetate:n-hexane=1:2), recrystallization from ethyl acetate-n-hexane to yield 1.0 g of methyl 4-(4-methylthiophenyl)-3(E)-butenyl 1,4-dihydro-2,6-dimethyl-4-(3-nitrophenyl)-yridine-3,5-dicarboxylate in the form of light yellow powdery substance. Melting point: 165°–170° C.

EXAMPLE 6

3.36 Grams of 1-[2(E)-acetoacetocymethylvinyl]-(4-(2-tetrahydropyranyloxy)benzene, 1.5 g of 3-nitrobenzaldehyde and 1.2 g of methyl 3-aminocrotonate were added to 20 ml of isopropanol, and the mixture was refluxed for 8 hours. The reaction mixture was concentrated and the residue was purified by means of a silica gel column chromatography (eluent: chloroform) to yield 1.2 g of methyl 3-(4-tetrahydropyranyloxyphenyl)-2(E)-propenyl 1,4-dihydro-2,6-dimethyl-4-(3-nitrophenyl)-pyridine-3,5-dicarboxylate.

N. M. R. $\delta$ (CDCl$_3$): 1.4–2.0 (6H, m), 2.26 (6H, m), 3.53 (3H, s), 3.4–4.0 (2H, m), 4.58 (2H, d, J=6 Hz), 5.03 (1H, s), 5.30 [1H, t, J=3 Hz), 5.97 (1H, dt, Ja=6 Hz, Jb=16H), 6.30 (1H, bs), 6.37 (1H, d, J=16 Hz), 6.88 (2H, d, J=9 Hz), 7.14 (2H, d, J=9 Hz), 7.20 (1H, t, J=6 Hz), 7.50 (1H, dt, Ja=2 Hz, Jb=6 Hz), 7.82 (1H, dt, Ja=2 Hz, Jb=6 Hz), 8.00 (1H, t, J=2 Hz).

EXAMPLES 7–30

By using a suitable starting material, and by methods similar to those described in Examples 1 and 6, there were prepared compounds as shown in Table 1 as follows.

TABLE 1

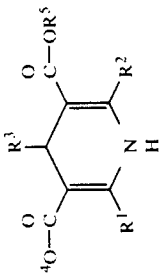

| Example No. | R¹ | R² | R³ | R⁴ | R⁵ | Melting point (°C.) (Recrystallization solvent) | Crystal form | Salt |
|---|---|---|---|---|---|---|---|---|
| 7 | $CH_3$ | $CH_3$ | m-$NO_2$-C₆H₄ | $CH_3$ | -CH₂-CH=CH-(4-HO-C₆H₄) | 137.5-139 (Ether-benzene) | Yellow powdery crystals IR[1] | — |
| 8 | $CH_3$ | $CH_3$ | m-$NO_2$-C₆H₄ | $CH_3$ | -CH₂-CH=CH-(3-HO-C₆H₄) | 60-63 (Ether-n-hexane) | Light yellow powdery crystals | — |
| 9 | $CH_3$ | $CH_3$ | m-$NO_2$-C₆H₄ | $CH_3$ | -CH₂-CH=CH-(2-HO-C₆H₄) | 75-105 (Ether-n-hexane) | Light yellow indefinite form crystals | — |
| 10 | $CH_3$ | $CH_3$ | m-$NO_2$-C₆H₄ | $CH_3$ | -CH₂-C(CH₃)=CH-(4-HO-C₆H₄) | 181-182 (Methanol) | Yellow powdery crystals | — |

TABLE 1-continued
| | | | | | | |
|---|---|---|---|---|---|---|
| 11 | CH₃ | 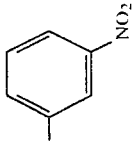 3-NO₂-phenyl | CH₃ | —CH₂C≡C—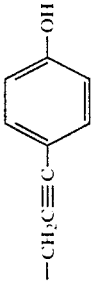—OH | 173-176 (Tetrahydrofuran-n-hexane) | Yellow prism-like crystals | — |
| 12 | CH₃ | 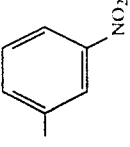 3-NO₂-phenyl | CH₃ | 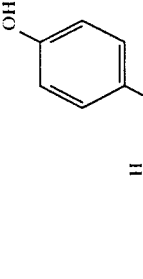 | 170-171 (Methanol) | Light yellow powdery crystals | — |
| 13 | CH₃ | 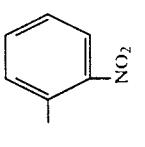 2-NO₂-phenyl | CH₃ | 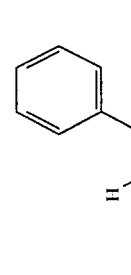 | 90-95 (Tetrahydrofuran-n-hexane) | Light yellow indefinite form crystals | — |
| 14 | CH₃ | 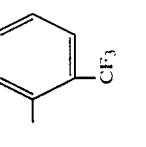 2-CF₃-phenyl | CH₃ | 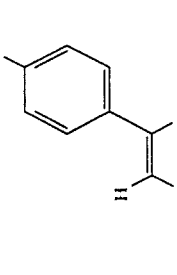 | 164-165 (Methanol-ether) | Light yellow powdery crystals | — |

TABLE 1-continued

| | | | | | | |
|---|---|---|---|---|---|---|
| 15 | CH$_3$ | CH$_3$ | 3-NO$_2$-C$_6$H$_4$ | CH$_3$ | 4-OH-3-OCH$_3$-C$_6$H$_3$-CH=CH-CH$_2$- (trans) | 146–153 (Isopropanol) | Yellow powdery crystals | — |
| 16 | CH$_3$ | CH$_3$ | 3-NO$_2$-C$_6$H$_4$ | CH$_3$ | 4-SCH$_3$-C$_6$H$_4$-CH=C(CH$_2$CH$_3$)- | 165–170 (Ethyl acetate-n-hexane) | Light yellow indefinite form crystals | — |
| 17 | CH$_3$ | CH$_3$ | 2-NO$_2$-C$_6$H$_4$ | CH$_3$ | 4-SCH$_3$-C$_6$H$_4$-CH=C(CH$_2$CH$_3$)- | 145–150 (Ethyl acetate-n-hexane) | Yellow indefinite form crystals | — |
| 18 | CH$_3$ | CH$_3$ | 3-NO$_2$-C$_6$H$_4$ | CH$_3$ | 4-OH-3-Cl-C$_6$H$_3$-CH=CH-CH$_2$- | 68–70 (Ether-n-hexane) | Light yellow powdery crystals | — |

TABLE 1-continued

| | | | | | | | | |
|---|---|---|---|---|---|---|---|---|
| 19 | CH₃ | CH₃ | [m-NO₂-phenyl] | CH₃ | [structure: 4-OCOCH₃-phenyl-CH=CH-CH₂-] | NMR[1] | Light yellow indefinite form crystals | — |
| 20 | CH₃ | CH₃ | [m-NO₂-phenyl] | CH₃ | [structure: 4-OTHP*-phenyl-CH=CH-CH₂-] | NMR[2] | Light yellow indefinite form crystals | — |
| 21 | CH₃ | CH₃ | [m-NO₂-phenyl] | CH₃ | [structure: 3-OCH₂OCH₃-phenyl-CH=CH-CH₂-] | NMR[3] | Light yellow indefinite form crystals | — |
| 22 | CH₃ | CH₃ | [m-NO₂-phenyl] | CH₃ | [structure: 4-OTHP*-phenyl-CH=CH-CH₂-] | NMR[4] | Light yellow indefinite form crystals | — |
| 23 | CH₃ | CH₃ | [m-NO₂-phenyl] | CH₃ | [structure: 4-OTHP*-phenyl-C≡C-CH₂-] | NMR[5] | Light yellow indefinite form crystals | — |

TABLE 1-continued

| | | | | | | |
|---|---|---|---|---|---|---|
| 24 | CH$_3$ | CH$_3$ | 3-NO$_2$-C$_6$H$_4$- | CH$_3$ | (CH$_2$=CH–CH=CH–C$_6$H$_5$, OTHP*) | NMR$^6$ | Light yellow indefinite form crystals | — |
| 25 | CH$_3$ | CH$_3$ | 2-NO$_2$-C$_6$H$_4$- | CH$_3$ | (–CH$_2$–CH=CH–C$_6$H$_4$–OTHP*) | NMR$^7$ | Yellow indefinite form crystals | — |
| 26 | CH$_3$ | CH$_3$ | 2-CF$_3$-C$_6$H$_4$- | CH$_3$ | (–CH$_2$–CH=CH–C$_6$H$_4$–OTHP*) | NMR$^8$ | Light yellow indefinite form crystals | — |
| 27 | CH$_3$ | CH$_3$ | 3-NO$_2$-C$_6$H$_4$- | CH$_3$ | (–CH$_2$–CH=CH–C$_6$H$_3$(OCH$_3$)–OTHP*) | NMR$^9$ | Light yellow indefinite form crystals | — |

TABLE 1-continued
| | | | | | |
|---|---|---|---|---|---|
| 28 | CH₃ | CH₃ |  | CH₃ | 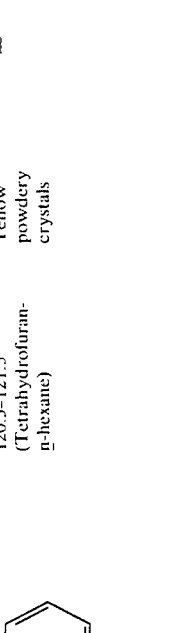 OCH₂OC₂H₅ | NMR¹⁰ | Light yellow indefinite form crystals | — |
| 29 | CH₃ | CH₃ | | CH₃ | | 120.5–121.5 (Tetrahydrofuran-n-hexane) | Yellow powdery crystals | — |
| 30 | CH₃ | CH₃ | | CH₃ | | 122–124 (Tetrahydrofuran-n-hexane) | Light yellow powdery crystals | — |
| 31 | CH₃ | CH₃ | | CH₃ | | 92–95 (Chloroform-n-hexane) | Light yellow powdery crystals | — |
| 32 | CH₃ | CH₃ | | CH₃ | OTHP* | NMR¹² | Yellow oily substance | — |

TABLE 1-continued

| | | | | | | |
|---|---|---|---|---|---|---|
| 33 | CH₃ | CH₃ | (phenyl) | CH₃ | (4-hydroxyphenyl-CH=C(H)-CH₂-) | 170-172 (Ether-n-hexane) | Light yellow prism-like crystals | — |
| 34 | CH₃ | CH₃ | (2-chlorophenyl) | CH₃ | (4-hydroxyphenyl-CH=C(H)-CH₂-) | 181-182 (Acetone) | Light yellow prism-like crystals | — |
| 35 | CH₃ | CH₃ | (2,4-dichlorophenyl) | CH₃ | (4-hydroxyphenyl-CH=C(H)-CH₂-) | 168-172 (Methanol) | Light yellow powdery crystals | — |
| 36 | CH₃ | CH₃ | (2-methylphenyl) | CH₃ | (4-hydroxyphenyl-CH=C(H)-CH₂-) | 175-177 (Tetrahydrofuran) | Light yellow powdery crystals | — |

TABLE 1-continued

| | | | | | | |
|---|---|---|---|---|---|---|
| 37 | CH₃ | ![3,4-dimethoxyphenyl] | CH₃ | ![4-hydroxyphenyl-CH=C(CH₃)-] | 197–198 (Acetone) | Light yellow powdery crystals | — |
| 38 | CH₃ | ![styryl-CH₂OCH₂] | CH₃ | ![phenyl-CH=C(CH₃)-] | 102.5–105 (Methylene chloride) | Light yellow powdery crystals | — |
| 39 | CH₃ | ![3-nitrophenyl] | C₂H₅ | ![4-hydroxyphenyl-CH=C(CH₃)-] | 145–148 (Methanol) | Light yellow prism-like crystals | — |
| 40 | CH₃ | ![3-nitrophenyl] | CH(CH₃)₂ | ![4-hydroxyphenyl-CH=C(CH₃)-] | 158–159 (Chloroform) | Light yellow powdery crystals | — |
| 41 | CH₃ | ![3-nitrophenyl] | CH₃ | ![CH₃-C(OH)=CH-] | 121–122 (Ether) | Light yellow powdery crystals | — |

TABLE 1-continued

| | | | | | | |
|---|---|---|---|---|---|---|
| 42 | CH₃ | 4-OH-C₆H₄-CH=CH-CH₂OCH₂- | 3-NO₂-C₆H₄ | CH₃ | CH₃ | 142-145 (Methanol) | Light yellow | ½H₂O |
| 43 | CH₃ | 4-OH-C₆H₄-CH=CH-CH₂OCH₂- | 2-Cl-C₆H₄ | CH₃ | CH₃ | 137-140 (Methanol) | Yellow powdery crystals | ½H₂O |
| 44 | CH₃ | 4-OH-C₆H₄-CH=CH-CH₂N(CH₃)CH₂- | 3-NO₂-C₆H₄ | CH₃ | CH₃ | 101.5-115 (Ethyl acetate-ether) NMR[13] | Yellow powdery crystals | HCl·H₂O |
| 45 | CH₃ | 3-NO₂-C₆H₄ | CH₃ | (tetrazolyl)-C(=CH-CH₃)- with N-CH₃ | | 194-196 (Methanol) | Light yellow needle-like crystals | — |
| 46 | CH₃ | 3-NO₂-C₆H₄ | CH₃ | (2-furyl)-C(=CH-CH₃)- | | 157-158 (Methanol) | Light yellow needle-like crystals | — |

TABLE 1-continued

| | | | | | |
|---|---|---|---|---|---|
| 47 | CH₃ | 3-NO₂-phenyl | CH₃ | —CH₂CH₂N(CH₃)—CH₂—C≡CH | 75-90 (Ether-n-hexane) NMR[14] | Light yellow powdery crystals | — |
| 48 | CH₃ | 3-NO₂-phenyl | CH₃ | —CH₂CH₂N(CH₃)—CH₂—C(H)=C(H)-phenyl | 82-85 (Ether-n-hexane) | Light yellow powdery crystals | — |
| 49 | CH₃ | 2-NO₂-phenyl | CH₃ | —CH₂CH₂N(CH₃)CH₂—C≡CH | 96-102 (Ether-n-hexane) | Light yellow powdery crystals | — |
| 50 | CH₃ | 3-NO₂-phenyl | CH₃ | —CH₂CH₂—S—CH₂—CH=CH-phenyl | 81.5-83 (Ethyl acetate-diisopropyl ether) | Light yellow powdery crystals | — |
| 51 | CH₃ | 3-NO₂-phenyl | CH₃ | —CH₂CH₂—O—CH₂—CH=CH-phenyl | 77.5-78.5 (Ethyl acetate-diisopropyl ether) | Light yellow powdery crystals | — |
| 52 | CH₃ | 3-NO₂-phenyl | CH₃ | —CH₂CH₂—S—CH₂C≡CH | NMR[15] | — | — |

TABLE 1-continued

| | | | | | | |
|---|---|---|---|---|---|---|
| 53 | CH₃ |  | CH₃ | —CH₂CH₂OCH₂C≡CH | NMR[16] | Light yellow indefinite form crystals | — |
| 54 | CH₃ |  | CH₃ |  | 115–116 (Ethyl acetate-diisopropyl ether) | Light yellow powdery crystals | — |
| 55 | CH₃ |  | CH₃ |  | 115–116 (Ethyl acetate-diisopropyl ether) | Light yellow powdery crystals | — |
| 56 | CH₃ |  | CH₃ |  | 168–169 (Acetone) | Light yellow powdery crystals | HCl |
| 57 | CH₃ |  | CH₃ |  | NMR[17] | Yellow indefinite form crystals | — |
| 58 | CH₃ |  | CH₃ |  | 154–158 (Chloroform-n-hexane) | Light yellow powdery crystals | 2HCl.H₂O |

TABLE 1-continued

| | | | | | | |
|---|---|---|---|---|---|---|
| 59 | 3-NO2-phenyl | CH3 | CH3 | —CH2CH2—N(piperazine)N—CH2C≡C-phenyl | 217–220 (Ethyl acetate-methanol-water) | 2HCl, Light yellow needle-like crystals |
| 60 | 3-NO2-phenyl | CH3 | CH3 | —CH2C≡C-(2-thienyl) | 62–68 NMR[18] | Yellow indefinite form crystals |
| 61 | 3-NO2-phenyl | CH3 | CH3 | —CH2C≡C-(2-pyridyl) | 144–146 (Diisopropyl ether-ethanol) | HCl, Light yellow powdery crystals |
| 62 | 3-NO2-phenyl | CH3 | CH3 | —CH2—C(=CH-CH2-OCH2OC2H5)(H)-C6H4-(4-) | NMR[19] | — |

*OTHP: 2-tetrahydropyranyloxy group
IR[1] 1660, 1680, 1700 cm⁻¹
NMR[1] (90MHz, CDCl3):
2.28 (3H, s), 2.35 (6H, s), 3.64 (3H, s), 4.67 (2H, d, J=7Hz), 5.12 (1H, s), 6.06 (1H, broad, s), 6.15 (1H, d, t, Ja=7H, Jb=16Hz), 6.50 (1H, d, J=16Hz), 7.03 (2H, d, J=8Hz), 7.30 (2H, d, J=8Hz), 7.32 (1H, dt, Ja=2Hz, Jb=8Hz), 7.63 (1H, d, t, Ja=2Hz, Jb=8Hz), 7.97 (1H, d, t, Ja=2Hz, Jb=8Hz), 8.12 (1H, t, J=2Hz)
NMR[2] (90MHz, CDCl3):
1.45–2.10 (6H, m), 2.30 (6H, t), 3.40–4.00 (2H, m), 3.56 (3H, s), 4.63 (2H, d, J=6Hz), 5.10 (1H, s), 5.37 (1H, t, J=3Hz), 6.17 (1H, d, t, Ja=6Hz, Jb=16Hz), 6.45 (1H, d, J=16Hz), 6.65–7.20 (4H, m), 7.30 (1H, t, J=7Hz), 7.62 (1H, d, t, Ja=2Hz, Jb=7Hz), 7.95 (1H, d, t, Ja=2Hz, Jb=7Hz), 8.13 (1H, t, J=2Hz)
NMR[3] (90MHz, CDCl3):
2.30 (3H, s), 2.32 (3H, s), 3.38 (3H, s), 3.53 (3H, s), 4.65 (2H, d, J=7Hz), 5.10 (1H, s), 5.13 (2H, s), 6.20 (1H, dt, Ja=6Hz, Jb=16Hz), 6.47 (1H, s), 6.87 (1H, d, J=16Hz), 6.87–7.48 (5H, m), 7.62 (1H, dt, Ja=2Hz, Jb=7Hz), 7.93 (1H, dt, Ja=2Hz, Jb=7Hz), 8.12 (1H, t, J=2Hz)
NMR[4] (90MHz, CDCl3):
1.50–1.95 (6H, m), 1.97 (3H, s), 2.32 (6H, s), 3.34–3.90 (1H, m), 3.53 (3H, s), 4.65 (2H, d, J=7Hz), 5.03 (1H, s), 5.33 (1H, t, J=3Hz), 5.70 (1H, t, J=7Hz), 5.95 (1H, broad, s), 6.97 (2H, d, J=9Hz), 7.23 (2H, d, J=9Hz), 7.28 (1H, d, t, Ja=7Hz), 7.58 (1H, d, t, Ja=2Hz, Jb=7Hz), 7.93 (1H, dt, Ja=2Hz, Jb=7Hz), 8.08 (1H, t, J=2Hz)
NMR[5] (90MHz, CDCl3):
1.30–2.0 (6H, m), 2.32 (6H, s), 3.53 (3H, s), 3.3–3.95 (2H, m), 4.79 (2H, s), 5.07 (1H, t, J=3Hz), 5.33 (1H, s), 6.02 (1H, s), 6.93 (2H, d, J=10Hz), 7.28 (2H, d, J=8Hz), 7.27 (1H, t, J=8Hz), 7.66 (1H, d, J=8Hz), 7.93 (1H, d, J=8Hz), 8.10 (1H, s)
NMR[6] (90MHz, CDCl3):
1.40–2.10 (6H, m), 2.32 (6H, s), 3.43 (3H, s), 3.20–3.85 (2H, m), 4.43 (2H, d, J=7Hz), 4.95 (1H, s), 5.23 (1H, t, J=3Hz), 5.04–5.80 (1H, m), 5.93–6.53 (3H, m), TABLE 1-continued 6.60 (1H, s), 6.87 (2H, d, J=10Hz), 7.20 (2H, d, J=10Hz), 7.23 (1H, t, J=8Hz), 7.53 (1H, d, t, Ja=2Hz, Jb=8Hz), 7.88 (H, d, t, Ja=2Hz, Jb=8Hz)
NMR⁷ (60MHz, CDCl₃):
1.40–2.0 (6H, m), 2.30 (3H, s), 2.33 (3H, s), 3.20–3.90 (2H, m), 3.60 (3H, s), 4.63 (2H, d, J=6Hz), 5.37 (1H, t, J=3Hz), 5.80 (1H, d, t, Ja=6Hz, Jb=16Hz), 6.80 (1H, s), 6.38 (1H, d, J=16Hz), 6.90 (2H, d, J=9Hz), 7.20 (2H, d, J=9Hz), 6.75–7.80 (4H, m)
NMR⁸ (90MHz, CDCl₃):
1.43–2.15 (6H, m), 2.30 (6H, s), 3.38 (3H, s), 3.20–3.80 (2H, m), 4.47 (2H, dd, Ja=3Hz, Jb=7Hz), 5.23 (1H, t, J=3Hz), 5.43 (1H, s), 6.83 (1H, broad, s), 5.94 (1H, dt, Ja=6Hz, Jb=16Hz), 6.23 (1H, d, J=9Hz), 6.87 (2H, d, J=9Hz), 7.13 (2H, d, J=9Hz), 6.75–7.60 (4H, m)
NMR⁹ (90MHz, CDCl₃):
1.5–2.1 (6H, m), 2.28 (3H, s), 3.53 (3H, s), 3.76 (3H, s), 3.4–4.1 (1H, m), 4.57 (2H, d, J=6Hz), 5.27 (1H, t, J=3Hz), 5.99 (1H, dt, Ja=6Hz, Jb=16Ha), 6.07 (1H, s), 6.36 (1H, d, J=16Hz), 6.73 (1H, d, J=7Hz), 6.78 (1H, s), 6.93 (1H, D, J=7Hz), 7.18 (1H, t, J=7Hz), 7.50 (1H, dt, Ja=2Hz, Jb=7Hz), 7.83 (1H, dt, Ja=2Hz, Jb=7Hz), 7.99 (1H, t, J=2Hz)
NMR¹⁰ (60MHz, CDCl₃):
1.24 (3H, t, J=7Hz), 2.37 (3H, s), 3.66 (3H, s), 3.79 (2H, q, J=7Hz), 4.70 (2H, d, J=6Hz), 5.16 (1H, s), 5.30 (2H, s), 5.91 (1H, broad, s), 6.10 (1H, dt, Ja=6Hz, Jb=16Hz), 6.40 (1H, d, J=16Hz), 7.00–7.47 (4H, m), 7.64 (1H, dt, Ja=2Hz, Jb=7Hz), 7.97 (1H, dt, Ja=2Hz, Jb=7Hz), 8.14 (1H, t, J=2Hz)
NMR¹¹ (90MHz, CDCl₃):
1.40–2.10 (6H, m), 2.26 (6H, m), 3.53 (3H, s), 3.40–4.0 (2H, m), 4.58 (2H, d, J=6Hz), 5.03 (1H, s), 5.30 (1H, t, J=3Hz), 5.97 (1H, dt, Ja=6Hz, Jb=16Hz), 6.30 (1H, broad, s), 6.37 (1H, d, J=16Hz), 6.88 (2H, d, J=9Hz), 7.14 (2H, d, J=9Hz), 7.20 (1H, t, J=6Hz), 7.50 (1H, dt, Ja=2Hz, Jb=6Hz), 7.82 (1H, dt, Ja=2Hz, Jb=6Hz), 8.00 (1H, t, J=2Hz)
NMR¹² (90MHz, CDCl₃):
1.5–2.1 (6H, m), 2.33 (6H, s), 2.48 (2H, q, J=6Hz), 3.58 (3H, s), 3.5–4.0 (2H, m), 4.15 (2H, t, J=6Hz), 5.09 (1H, s), 5.40 (1H, m), 5.93 (1H, d, t, J=15Hz, 6Hz), 6.30 (1H, s), 6.32 (1H, d, J=15Hz), 6.96 (2H, d, J=9Hz), 7.19 (2H, d, J=9Hz), 7.1–7.3 (1H, m), 7.5–7.7 (1H, d, m, J=6Hz), 7.8–8.0 (1H, D, m, J=6Hz), 8.10 (1H, m)
NMR¹³ (90MHz, CDCl₃):
2.36 (3H, s), 2.40 (3H, s), 3.25 (2H, d, J=6Hz), 3.63 (6H, s), 3.6–3.9 (2H), 5.10 (1H, s), 6.20 (1H, dt, J=16Hz, 6Hz), 6.53 (1H, d, J=16Hz), 5.75 (1H, bs), 7.20–8.20 (9H, m)
NMR¹⁴ (90MHz, CDCl₃):
2.36 (9H, s), 2.75 (2H, t, J=6Hz) 3.53 (2H, s), 3.62 (3H, s), 4.16 (2H, t, J=6Hz), 5.11 (1H, s), 5.11 (1H, s), 5.80 (1H, bs), 7.20–8.20 (9H, m)
NMR¹⁵ (90MHz, CDCl₃):
2.33 (6H, s), 2.93 (2H, t, J=6Hz), 3.48 (2H, s), 3.63 (3H, s), 4.30 (2H, t, J=6Hz), 5.11 (1H, s), 6.22 (1H, s), 7.20–7.50 (6H, m), 7.66 (1H, dt, J=8Hz, J=2Hz), 7.93 (1H, bd, J=8Hz), 8.12 (1H, t, J=2Hz)
NMR¹⁶ (90MHz, CDCl₃):
2.35 (6H, s), 3.60 (3H, s), 3.76 (2H, t, J=5Hz), 4.17–4.33 (2H, m), 4.36 (2H, s), 5.11 (1H, s), 5.80 (1H, bs), 7.20–8.20 (9H, m)
NMR¹⁷ (90MHz, CDCl₃):
2.20 (3H, s), 2.27 (3H, s), 2.30 (3H, s), 2.62 (2H, t, J=6Hz), 3.51 (3H, s), 4.18 (2H, m), 5.72 (1H, s), 5.82 (1H, bs), 6.18 (1H, dt, J=6Hz, J=16Hz), 6.43 (1H, d, J=16Hz), 7.10–7.55 (8H, m), 7.62 (1H, d, J=7.5Hz)
NMR¹⁸ (90MHz, CDCl₃):
2.37 (6H, s), 3.64 (3H, s), 4.87 (2H, s), 5.13 (1H, s), 6.20 (1H, brs), 6.94 (1H, dd, J=4.5Hz, J=4Hz), 7.1–7.4 (3H, m), 7.64 (1H, d-m, J=8Hz), 7.97 (1H, d-m J=8Hz), 8.10 (1H, t, J=2Hz)
NMR¹⁹ (90MHz, CDCl₃):
1.17 (3H, t, J=7Hz), 1.47 (3H, d, J=5.5Hz), 2.34 (6H, s), 3.35–3.95 (2H, m), 3.60 (3H, s), 4.65 (2H, d=6Hz), 5.10 (1H, s), 5.35 (1H, 2, J=5.2Hz), 6.05 (1H, dt, J=6Hz, 15.5Hz), 6.46 (1H, d, J=15.5Hz), 6.89 (2H, d, J=9Hz), 7.18–8.09 (6H, m)

EXAMPLE 63

By using suitable starting materials, by a method similar to that described in Example 3, there were prepared compounds of Examples 1 and 7-62.

EXAMPLE 64

By using suitable starting materials, by a method similar to that described in Example 5, there were prepared compounds of Examples 1 and 7-15, and 17-62.

EXAMPLE 65

0.5 Gram of methyl 3-(4-hydroxyphenyl)-2(E)-propenyl 1,4-dihydro-2,6-dimethyl-4-(3-nitrophenyl)-pyridine-3,5-dicarboxylate was dissolved in 5 ml of pyridine, then to this solution was added 0.5 ml of acetic anhydride under an ice-cooling condition. The reaction mixture was allowed to stand overnight, then poured into an ice-water, and extracted with ether. The ether layer was washed with a diluted hydrochloric acid, 10%-sodium bicarbonate aqueous solution and water in this order, then dried with anhydrous sodium sulfate. The ether extract was concentrate, and the residue thus obtained was purified by means of a silica gel column chromatography (eluent: methanol:chloroform=1:100) to yield 0.4 g of methyl 3(4-acetyloxyphenyl)-2(E)-propenyl 1,4-dihydro-2,6-dimethyl-4-(3-nitrophenyl)-pyridine-3,5-dicarboxylate in the form of light yellow indefinite form crystals.

NMR; 2.28 (3H, s), 2.35 [6H, s), 3.64 (3H, s), 4.67 (2H, d, J=7 Hz), 5.12 (1H, s), 6.06 (1H, broad S), 6.15 [1H, d, t, Ja=7 Hz, Jb=16 Hz), 6.50 (1H, d, J=16 Hz), 7.03 [2H, d, J=8 Hz), 7.30 (2H, d, J=8 Hz), 7.32 (1H, t, J=8 Hz), 7.63 (1H, dt, Ja=2 Hz, Jb=8 Hz), 7.97 (1H, d, t, Ja=2 Hz, Jb=8 Hz), 8.12 (1H, t, J=2H).

EXAMPLE 66

50 Grams of 4-(1-ethoxyethoxy)cinnamyl methyl 2,6-dimethyl-4-(3-nitrophenyl)-1,4-dihydropyridine was dissolved in 600 ml of tetrahydrofuran, the solution was cooled to 5° C., then 170 ml of 0.5N-hydrochloric acid was added in one time to the solution. After 1 hour, the temperature of the reaction mixture was kept at 10°-15° C., and the reaction mixture was stirred for 2 hours. Sodium chloride was added to the reaction mixture and the aqueous layer was removed, the 5%-sodium hydrogen carbonate aqueous solution was added to adjust the pH to 7.0-7.5. The aqueous layer was removed by separation, then the organic layer was washed with water, a saturated sodium chloride aqueous solution in the order, and dried with anhydrous magnesium sulfate. The dried organic layer was concentrated at 20°-25° C., the residue thus obtained was recrystallized from chloroform to yield 20 g of (4-hydroxy-phenyl)-2(E)-propenyl methyl 2,6-dimethyl-4-(3-1,4 -dihydropyridine-3,5-dicarboxylate. Melting point: 145.8°-149.4° C. IR: 1670 cm$^{-1}$.

In the above-mentioned Examples 66, the recrystallization was conducted by using ether in place of chloroform, there was yield (4-hydroxyphenyl)-2(E)-propenyl methyl 2,6-dimethyl-4-(3-nitrophenyl)-1,4-dihydropyridine-3,5-dicarboxylate having the melting point of 163°-164° C. IR: 1660 cm$^{-1}$, 1680 cm$^{-1}$.

EXAMPLE 67

3.0 Grams of 3-nitrobenzaldehyde, 2.3 g of methyl 3-aminocrotonate and 5 g of methyl 4(E)-cinnamyloxyacetoacetate were suspended in 15 ml of isopropanol, and the suspension was refluxed for 10 hours. After the reaction was finished, the solvent was removed by evaporation under a reduced pressure, and the residue thus obtained was purified by means of a silica gel column chromatography (eluent: ether:n-hexane=1:3 to 1:2). Recrystallization from ether to yield 4.0 g of 3,5-dimethyl 2-cinnamyloxy-6-methyl-4-(3-nitrophenyl)-3,5-dicarboxylate in the form of light yellow powdery substance. Melting point: 121°-122° C.

By a method similar to that described in Example 67, and by using suitable starting materials, there were prepared compounds of Examples 42-44.

EXAMPLE 68

5.1 Grams of 2-iodomethyl methyl 2,6-dimethyl-4-(3-nitrophenyl)-1,4-dihydropyridine-3,5-dicarboxylate, and 3.8 g of 4-phenyl-1,2,3,6-tetrahydropyridine were dissolved in 10 ml of toluene, and the solution was refluxed for 6 hours. After the reaction mixture was allowed to stand to cooled at a room temperature, the crystals precipitated in the reaction mixture were removed by filtration, the filtrate was concentrated and the residue thus obtained was dissolved in chloroform. The chloroform layer was washed with a saturated sodium hydrogen carbonate aqueous solution and water in this order, then dried with anhydrous sodium sulfate. Then the dried chloroform extract was concentrated by removing the solvent by evaporation, and the residue thus obtained was purified by means of a silica gel column chromatography (eluent: chloroform:methanol=300:1), and recrystallized from ethyl acetate-diisopropyl ether to yield 3.6 g of methyl 2-(4-phenyl-1,2,3,6-tetrahydropyridyl)ethyl 2,6-dimethyl-4-(3-nitrophenyl)-1,4-dihydropyridine-3,5-dicarboxylate in the form of light yellow powdery substance. Melting point: 115°-116° C.

By a method similar to that described in Example 68, and by using suitable starting materials, there were prepared compounds of Examples 47-59.

EXAMPLE 69

10.2 Grams of methyl 2-piperazinylethyl 2,6-dimethyl- 4-(3-nitrophenyl)-1,4-dihydropyridine-3,5-dicarboxylate and 4.5 g of 3-phenylpropargyl bromide in 100 ml of acetonitrile were stirred at 30° C. for 5 hours under heating condition. After the reaction was finished, chloroform was added to the reaction mixture, and the mixture was washed with a saturated sodium hydrogen carbonate aqueous solution and water in this order, and dried with anhydrous sodium sulfate. The dried chloroform extract was concentrated by removing the solvent by evaporation, the residue thus obtained was purified by means of a silica gel column chromatography (eluent: dichloromethane—methanol:-dichloromethane=1:100). The product thus purified was then converted into a hydrochloride by adding hydrochloric acid-dioxane, and recrystallized from ethyl acetate-methanol-water to yield 1.2 g of methyl 2-[4-(3-phenyl-2-propynyl)-1-piperazinyl]ethyl 2,6-dimethyl-4-(3-nitrophenyl)-1,4-dihydropyridine-3,5-dicarboxylate in the form of light yellow needle-like crystals. Melting point: 217°-220° C.

By a method similar to that described in Example 69, and by using a suitable starting material, there was prepared a compound of Example 58.

Pharmacological tests

The results of the pharmacological test on dihydropyridine derivatives of the present invention are shown below.

The test compounds used in the tests are as follows.
Test Compound No.
1. Methyl 3-(4-hydroxyphenyl)-2(E)-propenyl 1,4-dihydro-2,6dimethyl-4-(3-nitrophenyl)pyridine-3,5-dicarboxylate
2. Methyl 3-phenyl-2(E)-propenyl 1,4-dihydro-2,6-dimethyl-4-(3-nitrophenyl)pyridine-3,5-dicarboxylate
3. Methyl 5-(4-hydroxyphenyl)-2(E),4(E)-pentadienyl 1,4-dihydro-2,6-dimethyl-4-(3-nitrophenyl)-pyridine-3,5-dicarboxylate
4. Methyl 3-methyl-3-(4-hydroxyphenyl)-2(E)-propenyl 1,4-dihydro-2,6-dimethyl-4-(3-nitrophenyl)pyridine-3,5-dicarboxylate
5. Methyl 3-phenyl-2-propynyl 1,4-dihydro-2,6-dimethyl-4-(3-nitrophenyl)pyridine-3,5-dicarboxylate
6. Methyl 3-phenylpropyl 1,4-dihydro-2,6-dimethyl-4-(3-nitrophenyl)pyridine-3,5-dicarboxylate [Reference compound: Japanese Patent Application Kokai (Laid-open) No. 56-36455 (1981)]
7. Methyl 3-(3-methoxy-4-hydroxyphenyl)-2(E)-propenyl 1,4-dihydro-2,6-dimethyl-4-(3-nitrophenyl)pyridine-3,5-dicarboxylate
8. Methyl 3-(4-methoxyphenyl)-2(E)-propenyl 1,4-dihydro-2,6-dimethyl-4-(3-nitrophenyl)-pyridine-3,5-dihydrocarboxylate
9. Methyl 3-(1-methyl-1,2,3,4-tetrazol-5-yl)-2(E)-propenyl 1,4-dihydro-2,6-dimethyl-4-(3-nitrophenyl)pyridine-3,5-dicarboxylate
10. Methyl 3-furyl-2(E)-propenyl 1,4-dihydro-2,6-dimethyl-4-(3-nitrophenyl)pyridine-3,5-dicarboxylate
11. Methyl 3-(3-chloro-4-hydroxyphenyl)-2(E)-propenyl 1,4-dihydro-2,6-dimethyl-4-(3-nitrophenyl)pyridine-3,5-dicarboxylate
12. Methyl 3-(4-hydroxyphenyl)-2-propynyl 1,4-dihydro-2,6-dimethyl-4-(3-nitrophenyl)-pyridine-3,5-dicarboxylate
13. Methyl 3-(2-hydroxyphenyl)-2(E)-propenyl 1,4-dihydro-2,6-dimethyl-4-(3-nitrophenyl)-pyridine-3,5-dicarboxylate
14. Methyl 3-(4-hydroxyphenyl)-2(E)-propenyl 1,4-dihydro-2,6-dimethyl-4-(2-trifluoromethylphenyl)-pyridine-3,5-dicarboxylate
15. Methyl 4-(4-methylthiophenyl)-3(E)-butenyl 1,4-dihydro-2,6-dimethyl-4-(3-nitrophenyl)-pyridine-3,5-dicarboxylate
16. Methyl 3-(4-acetyloxyphenyl)-2(E)-propenyl 1,4-dihydro-2,6-dimethyl-4-(3-nitrophenyl)pyridine-3,5-dicarboxylate
17. Methyl 2-[4-(4-methylphenyl)-1,2,3,6-tetrahydropyridyl]ethyl 1,4-dihydro-2,6-dimethyl-(3-nitrophenyl)pyridine-3,5-dicarboxylate
18. Methyl 3-(4-hydroxyphenyl)-2(E)-propenyl 1,4-dihydro-2,6-dimethyl-4-phenylpyridine-3,5-dicarboxylate
19. Methyl 3-(4-hydroxyphenyl)-2(E)-propenyl 1,4-dihydro-2,6-dimethyl-4-(2-methylphenyl)-pyridine-3,5-dicarboxylate
20. Methyl 3-(4-hydroxyphenyl)-2(E)-propenyl 1,4-dihydro-2,6-dimethyl-4-(3,4-dimethoxyphenyl)pyridine-3,5-dicarboxylate
21. Dimethyl 1,4-dihydro-2-[3-(4-hydroxyphenyl)-2(E)-propenyloxymethyl]-6-methyl-4-(3-nitrophenyl)pyridine-3,5-dicarboxylate
22. Methyl 3-(2-thienyl)-2-propynyl 1,4-dihydro-2,6-dimethyl-4-(3-nitrophenyl)pyridine-3,5-dicarboxylate
23. Methyl 2-[4-(3-phenyl-2-propynyl)-1-piperazinyl]ethyl 1,4-dihydro-2,6-dimethyl-(3-nitrophenyl)pyridine-3,5-dicarboxylate
24. Methyl 3-(4-hydroxyphenyl)-2(E)propenyl 1,4-dihydro-2,6-dimethyl-4-(2,4-dichlorophenyl)pyridine-3,5-dicarboxylate
25. Methyl 3-(3-hydroxyphenyl)-2(E)propenyl 1,4-dihydro-2,6-dimethyl-4-(3-nitrophenyl)-pyridine-3,5-dicarboxylate
26. Methyl 2-(N-methyl-N-benzylamino)ethyl 1,4-dihydro-2,6-dimethyl-4-(3-nitrophenyl)pyridine-3,5-dicarboxylate [Reference compound known as "Nicardipine"]

Pharmacological test-1

Vasodilative effects of the dihydropyridine derivatives of the present invention were determined by measuring the systolic blood pressures of test animals before and after the administration of test compound.

Systolic blood pressures and heart beat of SHR-rats (spontaneously hypertensive rats) were determined by a "tail cuff method". Thus the test animal was placed in a thermostat chamber (Type: FR-12RS, manufactured by Isuze & Co.) and was warmed at 40° C. for 15 minutes so as to vasodilate the tail arteria, the systolic blood pressures were measured by an electro sphygmomanometer (Type: PE-300, manufactured by NarcoBiosystems, Inc.) and recorded by an ink-writing recorder (Type: RECTI-HORIZ 8s, manufactured by San-Ei Instrument & Co.). The experiments were conducted under non-anesthetized and semi-confinement conditions. The test compound was orally administered forcedly by using a sonde for oral administration. The test compound was suspended in 0.15%-gum arabic powder aqueous solution so as to make the quantity of the test compound to 2.5 ml/kg. The test animal was not fasted, and the systolic blood pressures (mm-Hg) were measured before the administration (hereinafter referred to as "PRE") and after the administration (8, 24, 30, 48, 54 and 72 hours after the administration) of the test compound. The data of systolic blood pressure measured before the administration are shown in absolute value of mmHg, and the data measured after the administration are shown in the differences from the absolute values. The results are shown in Table 2 as follows.

TABLE 2

| Test Compound No. | Dosage (mg/kg) p.o. | Blood pressure (mm-Hg) | | | | | |
|---|---|---|---|---|---|---|---|
| | | PRE | 8 | 24 | 30 | 48 | 54 | 72 |
| 1 | 30 | 195.0 | — | −41.0 | −52.0 | −26.5 | −19.8 | −12.5 |
| 2 | 30 | 187.4 | — | −38.6 | −21.2 | −21.0 | −19.2 | — |
| 3 | 30 | 180.8 | — | −31.0 | −30.8 | −15.6 | −12.6 | — |
| 4 | 30 | 184.4 | — | −18.0 | −25.8 | −19.8 | −14.6 | — |
| 5 | 30 | 180.8 | — | −75.4 | −66.8 | −20.8 | −10.6 | −9.6 |

TABLE 2-continued

| Test Compound No. | Dosage (mg/kg) p.o. | Blood pressure (mm-Hg) PRE | After the administration (Hours) 8 | 24 | 30 | 48 | 54 | 72 |
|---|---|---|---|---|---|---|---|---|
| 6 | 30 | 185.0 | −20.3 | +1.8 | — | — | — | — |

As can be seen the data shown in Table 2, the vasodilative effects of the dihydropyridine derivatives of the present invention can be prolonged for certain length of period as compared with that of the reference compounds.

Pharmacological tests

Calmodulin (calcium-dependent modulator protein) inhibitory activity of each of the test compounds was determined by judging from the difference between $IC_{50}$ (50%-inhibitory concentration) of calmodulin inhibitory activity of the test compound being measured in the presence of calmodulin together with calmodulin-dependent cyclic-AMP phosphodiesterase, and another $IC_{50}$ of calmodulin-dependent cyclic-AMP phosphodiesterase inhibitory activity of the same test compound being measured in the absence of calmodulin. In other words, calmodulin-specific-inhibitory activity of each of the test compounds was determined in case that the test compound shows higher inhibitory activity against calmodulin-dependent cyclic-AMP phosphodiesterase in the presence of calmodulin than another inhibitory activity against calmodulin-dependent cyclic-AMP phosphodiesterase only.

1) Reagents used in the test (1) Calmodulin: A calmodulin product manufactured by Amano & Co., which was isolated from the brain of bovine, and purified so as to be considered as a single substance with respect to SDS-page (polyacrylamide gel electrophoresis) method.

(2) Calmodulin-dependent cyclic-AMP phosphodiesterase (EC 3.1.4.17): An enzyme substance isolated from the heart of bovine and purified partially by a method of modified version of the disclosure in H. C. Ho, T. S. Teo, et al.: "Biochim. Biophys. Acta", 429, 461 (1976).

(3) 5'-Nucleotidase (EC 3.1.3.5): Grade IV substance (isolated from *Crotalus adamanteus* venom) manufactured by Sigma & Co.

(4) Others: Remainder of the reagents used in the test were those of reagent grade chemicals manufactured by Wako Pure-Chemical Industries, Ltd.

2) Method for the test

Calmodulin inhibitory activity of each of the test compounds was measured by a method of modified version of the disclosure in T. S. Teo and T. H. Wang: "J. Bio. Chem.", 248, 588 (1973).

(1) Cyclic-AMP-phosphodiesterase: One unit thereof hydrolyzes 1.0 micromole of 3':5'-cyclic-AMP to 5'-AMP per minute at pH 7.5 at 30° C., in the presence of a saturating level of calmodulin.

(2) Calmodulin: One unit thereof stimulates 0.015 activated unit of cyclic-AMP phosphodiesterase to of the maximum activity of the enzyme.

(3) 5'-Nucleotidase: One unit thereof hydrolyzes 1.0 micromole of inorganic phosphorus from adnosine 5'-monophosphate per minute at pH 9.0 at 37° C.

3) Reactions in the tests (1) Calmodulin-cyclic-AMP phosphodiesterase inhibitory activity:

40 mM of Imidazol, 20 mM of $MgCl_2$, 20 mM of $CaCl_2$, 0.008 unit of cyclic-AMP phosphodiesterase, 1.0 unit of calmodulin, 0.2 unit of 5'-nucleotidase and 1.0 ml of 10 mM-tris(hydroxymethyl)aminomethane/HCl buffer solution (pH 7.0) containing 0.5 mM of cyclic-AMP were mixed together, and reacted at 30° C. for 30 minutes. Each of the test compounds was dissolved in methanol or N,N-dimethylformamide as the solvent, provided that the quantity of the solvent was not exceed 2% of the total amount of the mixture. After the reaction was completed, the reaction mixture was ice-cooled, and 0.5 ml each of aqueous solutions of 16.5%-trichloroacetic acid, 1%-thiourea, 3%-ammonium ferrous sulfate were respectively added to the reaction mixture. Further, 0.15 ml of 4.4%-ammonium molibdate solution was added to the mixture and the whole of the mixture was stirred, and was centrifuged at 3,000 r.p.m. for 10 minutes. Then, the centrifuged mixture was allowed to stand at a room temperature for 20 minutes. The $OD_{660\ nm}$ (optical density at 660 nm) was measured.

(2) Cyclic-AMP phosphodiesterase inhibitory activity: The reaction was conducted by a method similar to that described in (1) as mentioned above, except that 1 mM of EGTA [ethylene glycol-bis($\beta$-amino ethyl ether)-N,N-tetraacetic acid] was used in place of 20 mM of $CaCl_2$. The reaction was conducted for 3 hours. The results are shown in Table 3 as follows.

TABLE 2

| Test Compound No. | Calmodulin-cyclic-AMP phosphodiesterase $IC_{50}$ (μg/ml) | Cyclic-AMP phosphodiesterase $IC_{50}$ (μg/ml) |
|---|---|---|
| 1 | 4.1 | 60 |
| 2 | 2.5 | >100 |
| 3 | 0.85 | >100 |
| 7 | 5.2 | 86 |
| 8 | 2.7 | >100 |
| 9 | 5.3 | 36 |
| 10 | 1.55 | >100 |
| 11 | 5.3 | 100 |
| 12 | 0.78 | 13 |
| 13 | 1.65 | 12.5 |
| 14 | 6.25 | >100 |
| 15 | 0.062 | 0.23 |
| 16 | 3.0 | 50 |
| 17 | 5.5 | >100 |
| 18 | 6.8 | 32 |
| 19 | 5.8 | 58 |
| 20 | 3.2 | 30 |
| 21 | 6 | >100 |
| 22 | 1.1 | >100 |
| 23 | 8.0 | >100 |
| 24 | 2.45 | 15 |
| 25 | 0.9 | 24.6 |
| 26 | 6.25 | 13 |

As can be seen from the data shown in Table 3. the dihydropyridine derivatives of the present invention have specific inhibitory activity against calmodulin as compared with that of indicated by known compound.

What is claimed is:

1. A dihydropyridine compound of the formula,

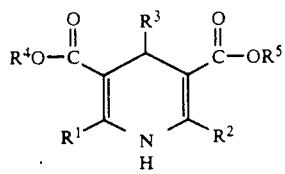

wherein $R^1$ and $R^2$ are both methyl; $R^4$ is a lower alkyl group; $R^3$ is a phenyl group which has 1 to 2 substituents selected from the group consisting of nitro group and a halogen atom; and $R^5$ is a group of the formula $-CH_2-A'-R^8$, wherein A' is a straight-chain or branched-chain unsaturated hydrocarbon group; and $R^8$ is a phenyl group, a thienyl group, or a furyl group.

2. The dihydropyridine compounds according to claim 1, wherein $R^8$ is an unsubstituted phenyl group.

3. The dihydropyridine compounds according to claim 2 or 1, wherein $R^3$ is a phenyl group which has 1 to 2 nitro groups as the substituents on the phenyl ring.

4. A hypotensive composition containing, as the active ingredient a dihydropyridine compound of claim 1 and pharmaceutically acceptable carriers.

5. Methyl 3-(4-hydroxyphenyl)-2(E)-propenyl 1,4-dihydro-2,6-dimethyl-4-(3-nitrophenyl)pyridine-3,5-dicarboxylate.

6. Methyl 3-phenyl-2(E)-propenyl 1,4-dihydro-2,6-dimethyl-4-(3-nitrophenyl)pyridine-3,5-dicarboxylate.

7. Methyl 3-phenyl-2-propynyl 1,4-dihydro-2,6-dimethyl-4-(3-nitrophenyl)-pyridine-3,5-dicarboxylate.

* * * * *